US009085659B2

(12) United States Patent
McManus et al.

(10) Patent No.: US 9,085,659 B2
(45) Date of Patent: Jul. 21, 2015

(54) POLYMER DERIVATIVES COMPRISING AN IMIDE BRANCHING POINT

(75) Inventors: Samuel P. McManus, Huntsville, AL (US); Antoni Kozlowski, Huntsville, AL (US)

(73) Assignee: Nektar Therapeutics, San Francisco, CA (US)

(*) Notice: Subject to any disclaimer, the term of this patent is extended or adjusted under 35 U.S.C. 154(b) by 1883 days.

(21) Appl. No.: 11/579,475

(22) PCT Filed: May 3, 2005

(86) PCT No.: PCT/US2005/015145
§ 371 (c)(1),
(2), (4) Date: Jul. 11, 2007

(87) PCT Pub. No.: WO2005/107815
PCT Pub. Date: Nov. 17, 2005

(65) Prior Publication Data
US 2008/0319091 A1 Dec. 25, 2008
US 2012/0238640 A9 Sep. 20, 2012

Related U.S. Application Data

(60) Provisional application No. 60/567,494, filed on May 3, 2004.

(51) Int. Cl.
| C08G 65/08 | (2006.01) |
| C08G 69/08 | (2006.01) |
| C07D 207/46 | (2006.01) |
| A61K 47/48 | (2006.01) |
| C08G 65/333 | (2006.01) |
| C08G 73/08 | (2006.01) |
| C08G 73/10 | (2006.01) |
| C08G 73/12 | (2006.01) |

(52) U.S. Cl.
CPC .... *C08G 65/33331* (2013.01); *A61K 47/48215* (2013.01); *A61K 47/48784* (2013.01); *C08G 73/08* (2013.01); *C08G 73/1092* (2013.01); *C08G 73/12* (2013.01)

(58) Field of Classification Search
CPC ........... A61K 47/48215; A61K 38/212; A61K 38/217; A61K 47/48246; A61K 8/86; C08G 77/46; C08G 77/388; C07C 237/30; C07C 237/08
USPC ................ 424/4, 422, 426, 244.1, 94.4, 94.3, 424/94.6; 514/772.1; 525/403, 54.1, 408; 530/816
See application file for complete search history.

(56) References Cited

U.S. PATENT DOCUMENTS 5,395,870 A 3/1995 Suzuki et al.
5,587,513 A * 12/1996 Pohmer et al. .................. 564/84
5,919,455 A * 7/1999 Greenwald et al. ........ 424/178.1
5,922,675 A 7/1999 Baker et al.
5,932,462 A 8/1999 Harris et al.
6,362,254 B2 3/2002 Harris et al.
7,053,150 B2 * 5/2006 Kozlowski et al. .......... 525/54.2
2002/0040076 A1 4/2002 Harris et al.
2002/0052443 A1 5/2002 Greenwald et al.

FOREIGN PATENT DOCUMENTS

| EP | 0 473 084 | 3/1992 |
| WO | 96/40749 | 12/1996 |
| WO | WO 98/35010 | 8/1998 |
| WO | WO 98/51784 | 11/1998 |
| WO | WO 02/44360 | 6/2002 |

OTHER PUBLICATIONS

Greene, et al., "Protective Groups in Organic Synthesis," 3$^{rd}$ Edition, John Wiley and Sons, Inc., New York (1999).
Harris, et al., *Nat. Rev. Drug Discov.*, vol. 2, No. 3, pp. 214-221 (2003).
Ouchi, et al., *Drug Des. Discov.*, vol. 9, No. 1, pp. 93-105 (1992).
Ouchi, et al., *Polymer Preprints*, vol. 38, No. 1, pp. 582-583 (1997).
Zalipsky, *Bioconjug. Chem.*, vol. 4, No. 4, pp. 296-299 (1993).
Sims, et al., *Anal. Biochem.*, vol. 107, pp. 60-63 (1980).
Bailon, et al., "Rational Design of a Potent, Long-Lasting Form of Interferon: A 40 kDa Branched Polyethylene Glycol-Conjugated Interferon α-2a for the Treatment of Hepatitis C", Bioconjugate Chem., vol. 12, pp. 195-202, (2001).
Holtsberg, et al., "Poly(ethylene glycol) (PEG) Conjugated Arginine Deiminase: Effects of PEG Formulations on its Pharmacological Properties", Journal of Controlled Release, vol. 80, pp. 259-271, (2002).
Klingshirn, et al., "Gelation of Ionic Liquids Using a Cross-Linked Poly(ethylene glycol) Gel Matrix", Chem. Mater., vol. 16, pp. 3091-3097, (2004).
Martinez, et al., "Branched Poly(ethylene glycol) linkers", Macromol. Chem. Phys., vol. 198, pp. 2489-2498, (1997).
PCT International Search Report and Written Opinion corresponding to PCT Application No. PCT/US2005/015145 mailed Apr. 13, 2007.
PCT International Preliminary Report on Patentability corresponding to PCT Application No. PCT/US2005/015145 mailed Jun. 7, 2007.

* cited by examiner

*Primary Examiner* — James J Seidleck
*Assistant Examiner* — S. Camilla Pourbohloul

(57) ABSTRACT

The invention provides a water-soluble polymer comprising (i) an imide group comprising a linking nitrogen atom, a first carbonyl group covalently attached to the linking nitrogen atom, and a second carbonyl group covalently attached to the linking nitrogen atom; (ii) a first water-soluble polymer segment covalently attached, either directly or through one or more atoms, to the first carbonyl group of the imide group and (iii) a second water-soluble polymer segment covalently attached, either directly or through one or more atoms, to the second carbonyl group of the imide group. The invention also provides, among other things, methods for preparing polymers, conjugates, pharmaceutical compositions and the like.

22 Claims, No Drawings

POLYMER DERIVATIVES COMPRISING AN IMIDE BRANCHING POINT

CROSS REFERENCE TO RELATED APPLICATIONS

This application is a 35 U.S.C. §371 application of International Application No. PCT/US2005/015145, filed May 3, 2005, designating the United States, which claims the benefit of priority under 35 U.S.C. §119(e) to U.S. Provisional Patent Application No. 60/567,494, filed May 3, 2004.

FIELD OF THE INVENTION

The present invention relates generally to branched polymer derivatives wherein branching in the polymer derivative is effected through an imide moiety. In addition, the invention relates to conjugates of the polymer derivatives, methods for synthesizing the polymer derivatives and methods for conjugating the polymer derivatives to active agents and other substances.

BACKGROUND OF THE INVENTION

Scientists and clinicians face a number of challenges in their attempts to develop active agents that are in a form suitable for delivery to a patient. Active agents that are polypeptides, for example, are often delivered via injection rather than orally. In this way, the polypeptide is introduced into the systemic circulation without exposure to the proteolytic environment of the stomach. Injection of polypeptides, however, has several drawbacks. For example, many polypeptides have a relatively short half-life, thereby necessitating repeated injections, which are often inconvenient and painful. Moreover, some polypeptides may elicit one or more immune responses with the consequence that the patient's immune system may be activated to degrade the polypeptide. Thus, delivery of active agents such as polypeptides is often problematic even when these agents are administered by injection.

Some success has been achieved in addressing the problems of delivering active agents via injection. For example, conjugating the active agent to a water-soluble polymer has resulted in polymer-active agent conjugates having reduced immunogenicity and antigenicity. In addition, these polymer-active agent conjugates often have greatly increased half-lives compared to their unconjugated counterparts as a result of decreased clearance through the kidney and/or decreased enzymatic degradation in the systemic circulation. As a result of having a greater half-life, the polymer-active agent conjugate requires less frequent dosing, which in turn reduces the overall number of painful injections and inconvenient visits with a health care professional. Moreover, active agents that were only marginally soluble demonstrate a significant increase in water solubility when conjugated to a water-soluble polymer.

Due to its documented safety and approval by the FDA for both topical and internal use, poly(ethylene glycol) has been conjugated to active agents. When an active agent is conjugated to polyethylene glycol or "PEG", the conjugated active agent is conventionally referred to as "PEGylated." The commercial success of PEGylated active agents, such as PEGASYS® PEGylated interferon alpha-2a (Hoffmann-La Roche, Nutley, N.J.), PEG-INTRON® PEGylated interferon alpha-2b (Schering Corp., Kenilworth, N.J.), NEULASTA™ PEG-filgrastim (Amgen Inc., Thousand Oaks, Calif.), demonstrates that administration of a conjugated form of an active agent can have significant advantages over the unconjugated counterpart. PEGylated versions of certain small molecules, such as distearoylphosphatidylethanolamine (Zalipsky (1993) *Bioconjug. Chem.* 4(4):296-299) and fluorouracil (Ouchi et al. (1992) *Drug Des. Discov.* 2(1):93-105), have also been prepared. Harris et al. have provided a review of the effects of PEGylation on pharmaceuticals. Harris et al. (2003) *Nat. Rev. Drug Discov.* 2(3):214-221.

Despite these successes, conjugation of a polymer to an active agent is often challenging. For example, attaching a relatively long poly(ethylene glycol) molecule to an active agent typically imparts greater water solubility than attaching a shorter poly(ethylene glycol) molecule. However, some conjugates bearing such long poly(ethylene glycol) moieties have been known to be substantially inactive in vivo. It has been hypothesized that these conjugates are inactive due to the length of the poly(ethylene glycol) chain, which effectively "wraps" itself around the entire active agent, thereby blocking access to potential ligands required for activity.

The problem associated with inactive conjugates bearing relatively large poly(ethylene glycol) moieties has been solved, in part, by using "branched" forms of a polymer derivative. "mPEG2-N-hydroxysuccinimide" and "mPEG2-aldehyde," as shown below, represent examples of branched versions of a poly(ethylene glycol) derivative.

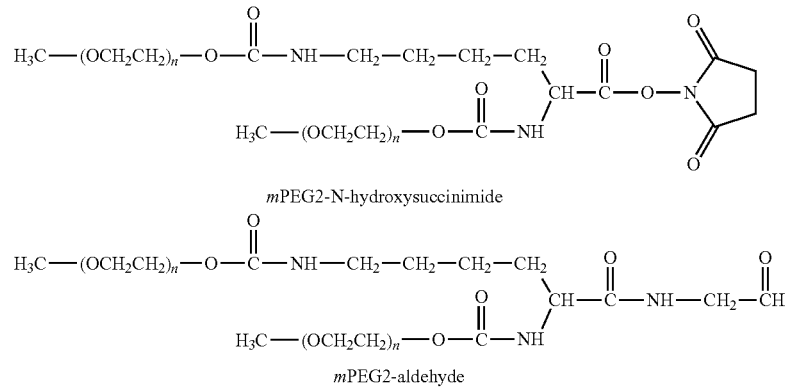

wherein n represents the number of repeating ethylene oxide monomer units.

Although solving some of the issues associated with using relatively large polymers, branched versions of polymer derivatives also have problems. For example, the increased structurally complexity of branching often results in a concomitant increase in synthetic complexity and/or purification difficulties. As a result, there is an ongoing need in the art for more readily synthesized and/or purified polymer derivatives that can be conveniently used in conjugation reactions with active agents.

SUMMARY OF THE INVENTION

In one or more aspects of the invention, a polymer is provided comprising a first water-soluble polymer segment and a second water-soluble polymer segment covalently linked, either directly or through a spacer moiety, to an imide moiety. The imide moiety serves as a branching point to which the two polymer segments are attached. Other groups, such as a reactive group, can also be attached to the imide moiety. As will be shown in further detail below, the imide moiety comprises two carbonyl groups, each of which is linked to a single nitrogen atom, herein referred to as a "linking nitrogen atom." Typically, the first and second water-soluble polymer segments are attached to the carbon atoms of the carbonyl groups, one water-soluble polymer segment per carbonyl group. In embodiments also comprising a reactive group, the reactive group is attached to the linking nitrogen atom, either directly or through one or more atoms. Thus, the various elements are attached in such as way as to result in a branched structure.

Attachment of the first and second water-soluble polymer segments, as well as the reactive group, to the imide moiety can be effected directly or indirectly. Direct attachment typically comprises a linkage—without any intervening atoms—between the imide moiety and the first or second water-soluble polymer segment or the reactive group. Indirect attachment comprises attachment of the polymer segment or reactive group to the imide moiety through a spacer moiety comprising one or more atoms. In some instances, both a direct and indirect attachment can be present within a single polymer.

Any water-soluble polymer segment and any reactive group can be used in the polymer and the invention is not limited in this regard. It is preferred, however, that the water-soluble polymer segments comprise poly(ethylene glycol). The polymer segments may include an end-capping moiety, such as alkoxy (e.g., methoxy or ethoxy), substituted alkoxy, alkenyloxy, substituted alkenyloxy, alkynyloxy, substituted alkynyloxy, aryloxy, substituted aryloxy, or hydroxy. In addition, preferred reactive groups include nucleophiles and electrophiles commonly used in synthetic organic chemistry. Particularly preferred reactive groups include hydroxyl (—OH), ester, orthoester, carbonate, acetal, aldehyde, aldehyde hydrate, ketone, vinyl ketone, ketone hydrate, thione, thione hydrate, hemiketal, sulfur-substituted hemiketal, ketal, alkenyl, acrylate, methacrylate, acrylamide, sulfone, amine, hydrazide, thiol, thiol hydrate, carboxylic acid, isocyanate, isothiocyanate, maleimide

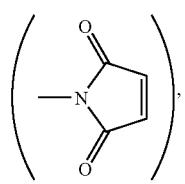

succinimide

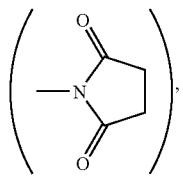

benzotriazole

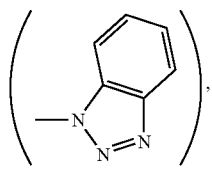

vinylsulfone, chloroethylsulfone, dithiopyridine, vinylpyridine, iodoacetamide, epoxide, glyoxals, diones, mesylates, tosylates, thiosulfonate, tresylate, and silane. Both water-soluble polymer segments and reactive groups suitable for use in connection with the present invention are discussed in more detail below.

In one or more embodiments, the polymer of the invention has one of the following structures:

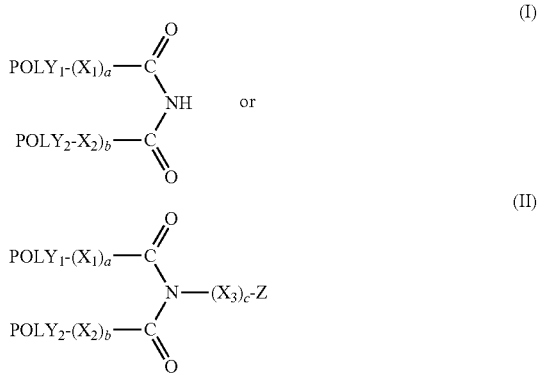

wherein:
POLY$_1$ is a first water-soluble polymer segment;
POLY$_2$ is a second water-soluble polymer segment;
each of (a), (b) and (c) is independently either zero or one;
X$_1$, when present, is a first spacer moiety;
X$_2$, when present, is a second spacer moiety;
X$_3$, when present, is a third spacer moiety; and
Z is a reactive group.

When present, each spacer moiety, X$_1$, X$_2$, and X$_3$, is preferably: a bivalent cycloalkyl group comprising 3 to about 20 carbon atoms; an amino acid; a C1-C10 alkylene group; —(CH$_2$)$_o$—Y—(CH$_2$)$_p$— wherein o and p are each independently zero to about 10 and Y is selected from the group consisting of —O—, —S—, —C(O)—, —C(S)—, —C(O)—O—, —C(O)—NH—, —NH—C(O)—NH—, —O—C(O)—NH—, and —N(R$_6$)— wherein R$_6$ is H or an organic radical selected from the group consisting of alkyl, substituted alkyl, alkenyl, substituted alkenyl, alkynyl, substituted alkynyl, aryl and substituted aryl; or a combination thereof, wherein the spacer moiety may optionally further include an ethylene oxide oligomer chain comprising 1 to 20 ethylene oxide monomer units.

In one or more aspects, the invention provides a method for preparing the polymers described herein. Briefly, the method comprises: (i) providing a first water-soluble polymer segment carrying a first reactive group that comprises a carbonyl group (C=O), (ii) reacting the first water-soluble polymer segment with anhydrous ammonia to form a water-soluble polymer intermediate carrying a terminal —C(O)—NH$_2$ group (iii) treating the water-soluble polymer intermediate with a strong base to remove a proton from the terminal —C(O)—NH$_2$ group, (iv) reacting the water-soluble polymer intermediate with a second water-soluble polymer segment carrying a second reactive group comprising a carbonyl group to form an imide-linked (—C(O)—NH—C(O)—) water-soluble polymer, the imide linking group comprising a linking nitrogen atom, a first carbonyl group covalently attached to the linking nitrogen atom, and a second carbonyl group covalently attached to the linking nitrogen atom, and (v) optionally, attaching a reactive group to the linking nitrogen atom of the imide-linked water-soluble polymer.

In one or more aspects, the invention provides a second method for preparing the polymers described herein. Briefly, the method comprises: (i) providing a first water-soluble polymer segment carrying a first reactive group, the first reactive group comprising a carbonyl group, (ii) reacting the first water-soluble polymer segment with a molecule comprising a second reactive group and an amine group, optionally separated by a spacer moiety, to form a water-soluble polymer intermediate comprising a —C(O)—NH— linkage between the water-soluble polymer segment and the second reactive group, (iii) treating the water-soluble polymer intermediate with a strong base to remove a proton from the nitrogen atom of the —C(O)—NH— linkage, and (iv) reacting the water-soluble polymer intermediate with a second water-soluble polymer segment carrying a third reactive group comprising a carbonyl group to form an imide-linked water-soluble polymer, the imide linking group comprising a linking nitrogen atom, a first carbonyl group covalently attached to the linking nitrogen atom, and a second carbonyl group covalently attached to the linking nitrogen atom.

In one or more aspects of the invention, an active agent-polymer conjugate is provided wherein the conjugate comprises a polymer as described herein covalently attached to an active agent. In addition, the invention also provides a method for forming active-agent conjugates wherein the method comprises the step of contacting a polymer as described herein to a pharmacologically active agent under conditions suitable to form a covalent attachment between the polymer and the pharmacologically active agent.

In one or more aspects of the invention, pharmaceutical compositions are provided comprising a polymer conjugate as described herein in combination with a pharmaceutically acceptable carrier. The pharmaceutical compositions encompass all types of formulations and in particular those that are suited for injection, e.g., powders that can be reconstituted as well as suspensions and solutions. Furthermore, the invention provides a method of treating a patient comprising the step of administering a polymer conjugate as described herein.

Additional aspects, advantages, and novel features of the invention will be set forth in the description that follows, and/or will become apparent to one having ordinary skill in the art upon the following, or may be learned by practice of the invention.

DETAILED DESCRIPTION OF THE INVENTION

Before describing the present invention in detail, it is to be understood that this invention is not limited to the particular polymers, synthetic techniques, active agents, and the like as such may vary.

It must be noted that, as used in this specification and the claims, the singular forms "a," "an," and "the" include plural referents unless the context clearly dictates otherwise. Thus, for example, reference to a "polymer" includes a single polymer as well as two or more of the same or different polymers, reference to a "conjugate" refers to a single conjugate as well as two or more of the same or different conjugates, reference to an "excipient" includes a single excipient as well as two or more of the same or different excipients, and the like.

In describing and claiming the present invention, the following terminology will be used in accordance with the definitions described below.

"PEG," "polyethylene glycol" and "poly(ethylene glycol)" as used herein, are meant to encompass any water-soluble poly(ethylene oxide). Typically, PEGs for use in accordance with the invention comprise the following structure "—O(CH$_2$CH$_2$O)$_m$—" where (m) is 2 to 4000. As used herein, PEG also includes "—CH$_2$CH$_2$—O(CH$_2$CH$_2$O)$_m$—CH$_2$CH$_2$—" and "—(CH$_2$CH$_2$O)$_m$—," depending upon whether or not the terminal oxygens have been displaced. When the PEG further comprises a spacer moiety (to be described in greater detail below), the atoms comprising the spacer moiety, when covalently attached to a water-soluble polymer segment, do not result in the formation of an oxygen-oxygen bond (i.e., an "—O—O—" or peroxide linkage). Throughout the specification and claims, it should be remembered that the term "PEG" includes structures having various terminal or "end capping" groups and so forth. The term "PEG" also means a polymer that contains a majority, that is to say, greater than 50%, of —CH$_2$CH$_2$O— monomeric subunits. With respect to specific forms, the PEG can take any number of a variety of molecular weights, as well as structures or geometries such as "branched," "linear," "forked," "multifunctional," and the like, to be described in greater detail below.

The terms "end-capped" or "terminally capped" are interchangeably used herein to refer to a terminal or endpoint of a polymer having an end-capping moiety. Typically, although not necessarily, the end-capping moiety comprises a hydroxy or C$_{1-20}$ alkoxy group. Thus, examples of end-capping moieties include alkoxy (e.g., methoxy, ethoxy and benzyloxy), as well as alkenyloxy, alkynyloxy, aryl, heteroaryl, cyclo, heterocyclo, and the like. In addition, saturated, unsaturated, substituted and unsubstituted forms of each of the foregoing are envisioned. Moreover, the end-capping group can also be a silane. The end-capping group can also advantageously comprise a detectable label. When the polymer has an end-capping group comprising a detectable label, the amount or location of the polymer and/or the moiety (e.g., active agent) of interest to which the polymer is coupled to can be determined by using a suitable detector. Such labels include, without limitation, fluorescers, chemiluminescers, moieties used in enzyme labeling, colorimetric (e.g., dyes), metal ions, radioactive moieties, and the like. Suitable detectors include photometers, films, spectrometers, and the like.

The term "water soluble" as in a "water-soluble polymer segment" and "water-soluble polymer" means any segment or polymer that is soluble in water at room temperature. Typically, a water-soluble polymer or segment will transmit at least about 75%, more preferably at least about 95% of light, transmitted by the same solution after filtering. On a weight basis, a water-soluble polymer or segment thereof will preferably be at least about 35% (by weight) soluble in water, more preferably at least about 50% (by weight) soluble in water, still more preferably about 70% (by weight) soluble in water, and still more preferably about 85% (by weight) soluble in water. It is most preferred, however, that the water-soluble polymer or segment is about 95% (by weight) soluble in water or completely soluble in water.

The term "non-peptidic" as in a "non-peptidic polymer" refers to a polymer substantially free of peptide linkages. However, the polymer may include a minor number of peptide linkages such as, for example, no more than about 1 peptide linkage per about 10 monomeric units.

Molecular weight in the context of a water-soluble polymer of the invention, such as PEG, can be expressed as either a number average molecular weight or a weight average molecular weight. Both molecular weight determinations, number average and weight average, can be measured using gel permeation chromatography or other liquid chromatography techniques. Other methods for measuring molecular weight values can also be used, such as the use of end-group analysis or the measurement of colligative properties (e.g., freezing-point depression, boiling-point elevation, or osmotic pressure) to determine number average molecular weight or the use of light scattering techniques, ultracentrifugation or viscometry to determine weight average molecular weight. The polymers of the invention are typically polydisperse (i.e., number average molecular weight and weight average molecular weight of the polymers are not equal), possessing low polydispersity values of preferably less than about 1.2, more preferably less than about 1.15, still more preferably less than about 1.10, yet still more preferably less than about 1.05, and most preferably less than about 1.03.

As used herein, the term "carboxylic acid" as in a "carboxylic acid" derivative is a moiety having a

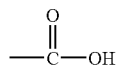

functional group [also represented as a "—COOH" or —C(O)OH]. Unless the context clearly dictates otherwise, the term carboxylic acid includes not only the acid form, but corresponding esters and protected forms as well. Exemplary protecting groups for carboxylic acids can be found in Greene et al., "PROTECTIVE GROUPS IN ORGANIC SYNTHESIS," 3$^{rd}$ Edition, John Wiley and Sons, Inc., New York, 1999.

The term "reactive" or "activated" when used in conjunction with a particular functional group, refers to a reactive functional group that reacts readily with an electrophile or a nucleophile on another molecule. This is in contrast to those groups that require strong catalysts or highly impractical reaction conditions in order to react (i.e., a "nonreactive" or "inert" group).

The terms "protected" or "protecting group" or "protective group" refer to the presence of a moiety (i.e., the protecting group) that prevents or blocks reaction of a particular chemically reactive functional group in a molecule under certain reaction conditions. The protecting group will vary depending upon the type of chemically reactive group being protected as well as the reaction conditions to be employed and the presence of additional reactive or protecting groups in the molecule, if any. Protecting groups known in the art can be found in Greene et al., supra.

As used herein, the term "functional group" or any synonym thereof is meant to encompass protected forms thereof.

The term "spacer" or "spacer moiety" is used herein to refer to an atom or a collection of atoms optionally used to link one moiety to another, such as a water-soluble polymer segment to a branching group such as an imide. The spacer moieties of the invention may be hydrolytically stable or may include a physiologically hydrolyzable or enzymatically degradable linkage.

"Alkyl" refers to a hydrocarbon chain, typically ranging from about 1 to 20 atoms in length. Such hydrocarbon chains are preferably but not necessarily saturated and may be branched or straight chain, although typically straight chain is preferred. Exemplary alkyl groups include ethyl, propyl, butyl, pentyl, 1-methylbutyl, 1-ethylpropyl, 3-methylpentyl, and the like. As used herein, "alkyl" includes cycloalkyl when three or more carbon atoms are referenced.

"Lower alkyl" refers to an alkyl group containing from 1 to 6 carbon atoms, and may be straight chain or branched, as exemplified by methyl, ethyl, n-butyl, iso-butyl, and tert-butyl.

"Cycloalkyl" refers to a saturated or unsaturated cyclic hydrocarbon chain, including bridged, fused, or spiro cyclic compounds, preferably made up of 3 to about 12 carbon atoms, more preferably 3 to about 8.

"Non-interfering substituents" are those groups that, when present in a molecule, are typically non-reactive with other functional groups contained within the molecule.

The term "substituted" as in, for example, "substituted alkyl," refers to a moiety (e.g., an alkyl group) substituted with one or more non-interfering substituents, such as, but not limited to: $C_3$-$C_8$ cycloalkyl, e.g., cyclopropyl, cyclobutyl, and the like; halo, e.g., fluoro, chloro, bromo, and iodo; cyano; alkoxy, lower phenyl (e.g., 0-2 substituted phenyl); substituted phenyl; and the like. "Substituted aryl" is aryl having one or more non-interfering groups as a substituent. For substitutions on a phenyl ring, the substituents may be in any orientation (i.e., ortho, meta, or para).

"Alkoxy" refers to an —O—R group, wherein R is alkyl or substituted alkyl, preferably $C_1$-$C_{20}$ alkyl (e.g., methoxy, ethoxy, propyloxy, benzyl, etc.), preferably $C_1$-$C_7$.

As used herein, "alkenyl" refers to a branched or unbranched hydrocarbon group of 1 to 15 atoms in length, containing at least one double bond, such as ethenyl, n-propenyl, isopropenyl, n-butenyl, isobutenyl, octenyl, decenyl, tetradecenyl, and the like.

The term "alkynyl" as used herein refers to a branched or unbranched hydrocarbon group of 2 to 15 atoms in length, containing at least one triple bond, e.g., ethynyl, n-propynyl, n-butynyl, isopentynyl, octynyl, decynyl, and so forth.

"Aryl" means one or more aromatic rings, each of 5 or 6 core carbon atoms. Aryl includes multiple aryl rings that may be fused, as in naphthyl or unfused, as in biphenyl. Aryl rings may also be fused or unfused with one or more cyclic hydrocarbon, heteroaryl, or heterocyclic rings. As used herein, "aryl" includes heteroaryl.

"Heteroaryl" is an aryl group containing from one to four heteroatoms, preferably N, O, or S, or a combination thereof. Heteroaryl rings may also be fused with one or more cyclic hydrocarbon, heterocyclic, aryl, or heteroaryl rings.

"Heterocycle" or "heterocyclic" means one or more rings of 5-12 atoms, preferably 5-7 atoms, with or without unsaturation or aromatic character and having at least one ring atom which is not a carbon. Preferred heteroatoms include sulfur, oxygen, and nitrogen.

"Substituted heteroaryl" is heteroaryl having one or more non-interfering groups as substituents.

"Substituted heterocycle" is a heterocycle having one or more side chains formed from non-interfering substituents.

"Electrophile" refers to an ion or atom or collection of atoms, that may be ionic, having an electrophilic center, i.e., a center that is electron seeking, or capable of reacting with a nucleophile.

"Nucleophile" refers to an ion or atom or collection of atoms, that may be ionic, having a nucleophilic center, i.e., a center that is seeking an electrophilic center or capable of reaction with an electrophile.

A "physiologically cleavable" or "hydrolyzable" or "degradable" bond is a relatively weak bond that reacts with water (i.e., is hydrolyzed) under physiological conditions. The tendency of a bond to hydrolyze in water will depend not only on the general type of linkage connecting two central atoms but also on the substituents attached to these central atoms. Appropriate hydrolytically unstable or weak linkages include, but are not limited to, carboxylate ester, phosphate ester, anhydrides, acetals, ketals, acyloxyalkyl ether, imines, ortho esters, peptides and oligonucleotides.

An "enzymatically degradable linkage" means a linkage that is subject to degradation by one or more enzymes.

A "hydrolytically stable" linkage or bond refers to a chemical bond, typically a covalent bond, that is substantially stable in water, that is to say, does not undergo hydrolysis under physiological conditions to any appreciable extent over an extended period of time. Examples of hydrolytically stable linkages include but are not limited to the following: carbon-carbon bonds (e.g., in aliphatic chains), ethers, amides, urethanes, and the like. Generally, a hydrolytically stable linkage is one that exhibits a rate of hydrolysis of less than about 1-2% per day under physiological conditions. Hydrolysis rates of representative chemical bonds can be found in most standard chemistry textbooks.

The terms "active agent," "biologically active agent" and "pharmacologically active agent" are used interchangeably herein and are defined to include any agent, drug, compound, composition of matter or mixture that provides some pharmacologic, often beneficial, effect that can be demonstrated in-vivo or in vitro. This includes foods, food supplements, nutrients, nutriceuticals, drugs, proteins, vaccines, antibodies, vitamins, and other beneficial agents. As used herein, these terms further include any physiologically or pharmacologically active substance that produces a localized or systemic effect in a patient.

"Pharmaceutically acceptable excipient" or "pharmaceutically acceptable carrier" refers to an excipient that can be included in the compositions of the invention and that causes no significant adverse toxicological effects to the patient.

"Pharmacologically effective amount," "physiologically effective amount," and "therapeutically effective amount" are used interchangeably herein to mean the amount of a polymer-active agent conjugate—typically present in a pharmaceutical preparation—that is needed to provide a desired level of active agent and/or conjugate in the bloodstream or in a target tissue. The exact amount will depend upon numerous factors, e.g., the particular active agent, the components and physical characteristics of the pharmaceutical preparation, intended patient population, patient considerations, and the like, and can readily be determined by one of ordinary skill in the art, based upon the information provided herein and available in the relevant literature.

"Multifunctional" in the context of a polymer of the invention means a polymer having 3 or more functional groups contained therein, where the functional groups may be the same or different. Multifunctional polymers of the invention will typically contain from about 3-100 functional groups, e.g., from 3-50 functional groups, from 3-25 functional groups, from 3-15 functional groups, and from 3 to 10 functional groups i.e., 3, 4, 5, 6, 7, 8, 9 or 10 functional groups) within the polymer. A "difunctional" polymer means a polymer having two functional groups contained therein, either the same (i.e., homodifunctional) or different (i.e., heterodifunctional).

"Branched," in reference to the geometry or overall structure of a polymer, refers to a polymer having 2 or more polymer "arms." A branched polymer may possess 2 polymer arms, 3 polymer arms, 4 polymer arms, 6 polymer arms, 8 polymer arms or more. One particular type of highly branched polymer is a dendritic polymer or dendrimer, which, for the purposes of the invention, is considered to possess a structure distinct from that of a branched polymer.

A "dendrimer" or dendritic polymer is a globular, size monodisperse polymer in which all bonds emerge radially from a central focal point or core with a regular branching pattern and with repeat units that each contribute a branch point. Dendrimers exhibit certain dendritic state properties such as core encapsulation, making them unique from other types of polymers.

A basic or acidic reactant described herein includes neutral, charged, and any corresponding salt forms thereof.

The term "patient," refers to a living organism suffering from or prone to a condition that can be prevented or treated by administration of a conjugate as provided herein, and includes both humans and animals.

"Optional" and "optionally" mean that the subsequently described circumstance may or may not occur, so that the description includes instances where the circumstance occurs and instances where it does not.

As used herein, the "halo" designator (e.g., fluoro, chloro, iodo, bromo, and so forth) is generally used when the halogen is attached to a molecule, while the suffix "ide" (e.g., fluoride, chloride, iodide, bromide, and so forth) is used when the ionic form is used when the halogen exists in its independent ionic form (e.g., such as when a leaving group leaves a molecule).

In the context of the present discussion, it should be recognized that the definition of a variable provided with respect to one structure or formula is applicable to the same variable repeated in a different structure, unless the context dictates otherwise. Thus, for example, the definition of "POLY," "a spacer moiety," and so forth with respect to a polymer can be equally applicable to a water-soluble polymer conjugate provided herein.

Turning to a first aspect of the invention, a polymer is provided comprising an imide moiety comprising the following structure:

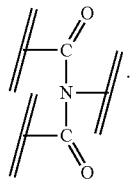

As shown, the imide moiety comprises a central linking nitrogen atom that is covalently bonded to the carbon atoms of two carbonyl groups.

In addition to the imide moiety, the polymer of the invention also comprises a first water-soluble polymer segment and a second water-soluble polymer segment. Each water-soluble polymer segment is attached, either directly or through a spacer moiety, to one of the two carbonyl groups attached to the linking nitrogen atom in the imide moiety, one water-soluble polymer segment per carbonyl group. Thus, the first and second water-soluble polymer segments are attached to the imide moiety as shown below.

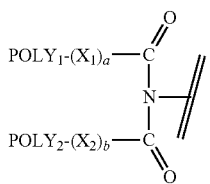

wherein:
POLY$_1$ is a first water-soluble polymer segment;
POLY$_2$ is a second water-soluble polymer segment;
each of (a) and (b) is independently either zero or one;
X$_1$, when present, is a first spacer moiety; and
X$_2$, when present, is a second spacer moiety.

Each of the first and second water-soluble polymer segments can comprise any polymer so long as the polymer is water-soluble. Moreover, a water-soluble polymer segment as used herein is typically non-peptidic. Although preferably a poly(ethylene glycol), (i.e., "PEG" or a "PEG polymer") a water-soluble polymer segment for use herein can be, for example, other poly(alkylene glycols) [e.g., poly(propylene glycol) ("PPG"), copolymers of ethylene glycol and propylene glycol and the like], poly(olefinic alcohol), poly(vinyl pyrrolidone), poly(hydroxyalkylmethacrylamide), poly(hydroxyalkylmethacrylate), poly(saccharides), poly(α-hydroxy acid), poly(vinyl alcohol), polyphosphazene, polyoxazoline, poly(oxyethylated polyol), and poly(N-acryloylmorpholine) such as described in U.S. Pat. No. 5,629,384. The polymer segments can be homopolymers of any of the foregoing polymers, random copolymers, block copolymers, alternating copolymers, random tripolymers, block tripolymers, alternating tripolymers and the like. In addition, a water-soluble polymer segment is often linear, but can be in other forms (e.g., branched, forked, and the like) as will be described in further detail below. In the context of being present within an overall structure, a water-soluble polymer segment has from 1 to about 300 termini.

Each water-soluble polymer segment in the overall structure can be the same or different. It is preferred, however, that all water-soluble polymer segments in the overall structure are of the same type. For example, it is preferred that all of the water-soluble polymer segments within a given structure are poly(ethylene glycol).

Although the number average molecular weight and weight average molecular weight of any individual water-soluble polymer segment can vary, both molecular weight values will typically be in one or more of the following ranges: from about 100 Daltons to about 100,000 Daltons; from about 500 Daltons to about 80,000 Daltons; from about 1,000 Daltons to about 50,000 Daltons; from about 2,000 Daltons to about 25,000 Daltons; from about 5,000 Daltons to about 20,000 Daltons. Exemplary number average molecular weights and weight average molecular weights for the water-soluble polymer segment include about 1,000 Daltons, about 5,000 Daltons, about 10,000 Daltons, about 15,000 Daltons, about 20,000 Daltons, about 25,000 Daltons, and about 30,000 Daltons.

Each water-soluble polymer segment is typically biocompatible and non-immunogenic. With respect to biocompatibility, a substance is considered biocompatible if the beneficial effects associated with use of the substance alone or with another substance (e.g., an active agent) in connection with living tissues (e.g., administration to a patient) outweighs any deleterious effects as evaluated by a clinician, e.g., a physician. With respect to non-immunogenicity, a substance is considered non-immunogenic if use of the substance alone or with another substance in connection with living tissues does not produce an immune response (e.g., the formation of antibodies) or, if an immune response is produced, that such a response is not deemed clinically significant or important as evaluated by a clinician. It is particularly preferred that the polymers and water-soluble polymer segments, described herein as well as conjugates of active agents and the polymers are biocompatible and non-immunogenic.

In one form useful in the present invention, free or non-bound PEG is a linear polymer terminated at each end with hydroxyl groups:

wherein (m') typically ranges from zero to about 4,000, preferably from about 20 to about 1,000.

The above polymer, alpha-,omega-dihydroxylpoly(ethylene glycol), can be represented in brief form as HO-PEG-OH where it is understood that the -PEG- symbol represents the following structural unit:

where (m') is as defined above.

Another type of free or nonbound PEG useful in the present invention is methoxy-PEG-OH, or MPEG in brief, in which one terminus is the relatively inert methoxy group, while the other terminus is a hydroxyl group. The structure of MPEG is given below.

where (m') is as described above.

Multi-armed or branched PEG molecules, such as those described in U.S. Pat. No. 5,932,462, can also be used as the PEG polymer. For example, PEG can have the structure:

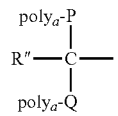

wherein:
poly$_a$ and poly$_b$ are PEG backbones (either the same or different), such as methoxy poly(ethylene glycol);
R" is a nonreactive moiety, such as H, methyl or a PEG backbone; and
P and Q are nonreactive linkages. In a preferred embodiment, the branched PEG polymer is methoxy poly(ethylene glycol) disubstituted lysine.

In addition, the PEG can comprise a forked PEG. An example of a free or nonbound forked PEG is represented by the following structure:

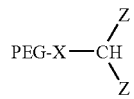

wherein: X is a spacer moiety and each Z is an activated terminal group linked to CH by a chain of atoms of defined length. U.S. Pat. No. 6,362,254 discloses various forked PEG structures capable of use in the present invention. The chain of atoms linking the Z functional groups to the branching carbon atom serve as a tethering group and may comprise, for example, alkyl chains, ether chains, ester chains, amide chains and combinations thereof.

The PEG polymer may comprise a pendant PEG molecule having reactive groups, such as carboxyl, covalently attached along the length of the PEG rather than at the end of the PEG chain. The pendant reactive groups can be attached to the PEG directly or through a spacer moiety, such as an alkylene group.

In addition to the above-described forms of PEG, the polymer can also be prepared with one or more weak or degradable linkages in the polymer, including any of the above described polymers. For example, PEG can be prepared with ester linkages in the polymer that are subject to hydrolysis. As shown below, this hydrolysis results in cleavage of the polymer into fragments of lower molecular weight:

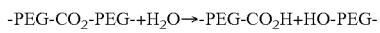

-PEG-CO$_2$-PEG-+H$_2$O→-PEG-CO$_2$H+HO-PEG-

Other hydrolytically degradable linkages, useful as a degradable linkage within a polymer backbone, include carbonate linkages; imine linkages resulting, for example, from reaction of an amine and an aldehyde (see, e.g., Ouchi et al. (1997) *Polymer Preprints* 38(1):582-3); phosphate ester linkages formed, for example, by reacting an alcohol with a phosphate group; hydrazone linkages which are typically formed by reaction of a hydrazide and an aldehyde; acetal linkages that are typically formed by reaction between an aldehyde and an alcohol; ortho ester linkages that are, for example, formed by reaction between a formate and an alcohol; amide linkages formed by an amine group, e.g., at an end of a polymer such as PEG, and a carboxyl group of another PEG chain; urethane linkages formed from reaction of, e.g., a PEG with a terminal isocyanate group and a PEG alcohol; and oligonucleotide linkages formed by, for example, a phosphoramidite group, e.g., at the end of a polymer, and a 5' hydroxyl group of an oligonucleotide.

It is understood by those of ordinary skill in the art that the term poly(ethylene glycol) or PEG represents or includes all the above forms of PEG.

Those of ordinary skill in the art will recognize that the foregoing discussion concerning substantially water-soluble polymers is by no means exhaustive and is merely illustrative, and that all polymeric materials having the qualities described above are contemplated. As used herein, the "term water-soluble polymer" generally refers to an entire molecule, which can comprise functional groups such as hydroxyl groups, thiol groups, ortho ester functionalities and so forth. The term water-soluble polymer segment is generally reserved for use in discussing specific molecular structures wherein the polymer is but one part of the overall molecular structure.

As depicted in the above formula, each water-soluble polymer segment is optionally attached to the rest of the structure through a spacer moiety. A spacer moiety is any atom or series of atoms connecting one part of a molecule to another. For purposes of the present disclosure, however, a series of atoms is not a spacer moiety when the series of atoms is immediately adjacent to a polymer and the series of atoms is but another monomer or oligomer such that the proposed spacer moiety would represent a mere extension of the polymer chain. For example, given the partial structure "POLY-X—," and POLY is defined as "CH$_3$O(CH$_2$CH$_2$O)$_m$—" wherein (m) is 2 to 4000 and X is defined as a spacer moiety, the spacer moiety cannot be defined as "—CH$_2$CH$_2$O—" since such a definition would merely represent an extension of the polymer. In such a case, however, an acceptable spacer moiety could be defined as "—CH$_2$CH$_2$—."

Each spacer moiety described herein, such as X$_1$ and X$_2$, is preferably: a bivalent cycloalkyl group comprising 3 to about 20 carbon atoms; an amino acid; a C1-C10 alkylene group; —(CH$_2$)$_o$—Y—(CH$_2$)$_p$— wherein o and p are each independently zero to about 10 and Y is selected from the group consisting of —O—, —S—, —C(O)—, —C(S)—, —C(O)—O—, —C(O)—NH—, —NH—C(O)—NH—, —O—C(O)—NH—, and —N(R$_6$)— wherein R$_6$ is H or an organic radical selected from the group consisting of alkyl, substituted alkyl, alkenyl, substituted alkenyl, alkynyl, substituted alkynyl, aryl and substituted aryl; and any combinations of two or more of the above-described spacer moieties. Additionally, any of the above spacer moieties may further include an ethylene oxide oligomer chain comprising 1 to 20 ethylene oxide monomer units, although as noted above, the oligomer chain would not be considered part of the spacer moiety if the oligomer is adjacent to a polymer segment and merely represents and extension of the polymer segment. Particularly preferred examples of spacer moieties include, but are not limited to, —C(O)—, —C(O)—NH—, —NH—C(O)—NH—, —O—C(O)—NH—, —C(S)—, —CH$_2$—, —CH$_2$—CH$_2$—, —CH$_2$—CH$_2$—CH$_2$—, —CH$_2$—CH$_2$—CH$_2$—CH$_2$—, —O—CH$_2$—, —CH$_2$—O—, —O—CH$_2$—CH$_2$—, —CH$_2$—O—CH$_2$—, —CH$_2$—CH$_2$—O—, —O—CH$_2$—CH$_2$—CH$_2$—, —CH$_2$—O—CH$_2$—CH$_2$—, —CH$_2$—CH$_2$—O—CH$_2$—, —CH$_2$—CH$_2$—CH$_2$—O—, —O—CH$_2$—CH$_2$—CH$_2$—CH$_2$—, —CH$_2$—O—CH$_2$—CH$_2$—CH$_2$—, —CH$_2$—CH$_2$—O—CH$_2$—CH$_2$—, —CH$_2$—CH$_2$—CH$_2$—O—CH$_2$—, —CH$_2$—CH$_2$—CH$_2$—CH$_2$—O—, —C(O)—NH—CH$_2$—, —C(O)—NH—CH$_2$—CH$_2$—, —CH$_2$—C(O)—NH—CH$_2$—, —CH$_2$—CH$_2$—C(O)—NH—, —C(O)—NH—CH$_2$—CH$_2$—CH$_2$—, —CH$_2$—C(O)—NH—CH$_2$—CH$_2$—, —CH$_2$—CH$_2$—C(O)—NH—CH$_2$—, —CH$_2$—CH$_2$—CH$_2$—C(O)—NH—, —C(O)—NH—CH$_2$—CH$_2$—CH$_2$—CH$_2$—, —CH$_2$—C(O)—NH—CH$_2$—CH$_2$—CH$_2$—, —CH$_2$—CH$_2$—C(O)—NH—CH$_2$—CH$_2$—, —CH$_2$—CH$_2$—CH$_2$—C(O)—NH—CH$_2$—, —CH$_2$—CH$_2$—CH$_2$—CH$_2$—C(O)—NH—, —C(O)—O—CH$_2$—, —CH$_2$—C(O)—O—CH$_2$—, —CH$_2$—CH$_2$—C(O)—O—CH$_2$—, —C(O)—O—CH$_2$—CH$_2$—, —NH—C(O)—CH$_2$—, —CH$_2$—NH—C(O)—CH$_2$—, —CH$_2$—CH$_2$—NH—C(O)—CH$_2$—, —NH—C(O)—CH$_2$—CH$_2$—, —CH$_2$—NH—C(O)—CH$_2$—CH$_2$—, —CH$_2$—CH$_2$—NH—C(O)—CH$_2$—CH$_2$—, —NH—C(O)—CH$_2$—CH$_2$—, —C(O)—NH—CH$_2$—, —C(O)—NH—CH$_2$—CH$_2$—, —O—C(O)—NH—CH$_2$—, —O—C(O)—NH—CH$_2$—CH$_2$—, —NH—CH$_2$—, —NH—CH$_2$—CH$_2$—, —CH$_2$—NH—CH$_2$—, —CH$_2$—CH$_2$—NH—CH$_2$—, —C(O)—CH$_2$—, —C(O)—CH$_2$—CH$_2$—, —CH$_2$—C(O)—CH$_2$—, —CH$_2$—CH$_2$—C(O)—CH$_2$—, —CH$_2$—CH$_2$—C(O)—CH$_2$—CH$_2$—, —CH$_2$—CH$_2$—C(O)—, —CH$_2$—CH$_2$—CH$_2$—C(O)—NH—CH$_2$—CH$_2$—NH—, —CH$_2$—CH$_2$—CH$_2$—C(O)—NH—CH$_2$—CH$_2$—NH—C(O)—, —CH$_2$—CH$_2$—CH$_2$—C(O)—NH—CH$_2$—CH$_2$—NH—C(O)—CH$_2$—, —CH$_2$—CH$_2$—NH—C(O)—CH$_2$—, —CH$_2$—CH$_2$—CH$_2$—C(O)—NH—CH$_2$—CH$_2$—NH—C(O)—CH$_2$—CH$_2$—, —O—C(O)—NH—(CH$_2$)$_h$—(OCH$_2$CH$_2$)$_j$—, —NH—C(O)—O—(CH$_2$)$_h$—(OCH$_2$CH$_2$)$_j$—, —O—, —S—, —N(R$_6$)—, and combinations of two or more of any of the foregoing, wherein (h) is zero to six, and (j) is zero to 20. Other specific spacer moieties have the following structures: —C(O)—NH—(CH$_2$)$_{1-6}$—NH—C(O)—, —NH—C(O)—NH—(CH$_2$)$_{1-6}$—NH—C(O)—, and —O—C(O)—NH—(CH$_2$)$_{1-6}$—NH—C(O)—, wherein the subscript values following each methylene indicate the number of methylenes contained in the structure, e.g., (CH$_2$)$_{1-6}$ means that the structure can contain 1, 2, 3, 4, 5 or 6 methylenes. Additionally, any of the above spacer moieties may further include an ethylene oxide oligomer chain comprising 1 to 20 ethylene oxide monomer units, although as noted above, the oligomer chain would not be considered part of the spacer moiety if the oligomer is adjacent to a polymer segment and merely represents and extension of the polymer segment.

In the present context of an amino acid being included in the structures provided herein, it should be remembered that the amino acid is connected to the rest of the structure via one, two, three or more sites. For example, a spacer moiety can result when an amino acid is attached to the rest of the molecule via two covalent attachments. In addition, a branching structure can result when an amino acid is attached to the rest of the molecule via three sites. Thus, the amino acid structure necessarily changes somewhat due to the presence of one or more covalent attachments (e.g., removal of a hydrogen atom from the amino acid in order to accommodate a covalent linkage). Consequently, reference to an "amino acid" therefore includes the amino acid containing one or more linkages to other atoms. The amino acid can be selected from the group consisting of alanine, arginine, asparagines, aspartic acid, cysteine, glutamic acid, glutamine, glycine, histidine, isoleucine, leucine, lysine, methionine, phenylalanine, proline, serine, threonine, tryptophan, tyrosine, and valine. Both the D and L forms of the amino acids are contemplated.

Each spacer moiety, when present, in the overall structure can be the same or different than any other spacer moiety in the overall structure. With respect to $X_1$ and $X_2$, it is preferred that $X_1$ and $X_2$ are the same when both are present in the polymer. As depicted in the formula, the linking moiety "$X_1$" is present when (a) is defined as one and absent when (a) is defined as zero. Similarly, the linking moiety "$X_2$" is present when (b) is defined as one and absent when (b) is defined as zero. Preferred spacer moieties corresponding to $X_1$ and/or $X_2$ include —$CH_2$—, —$CH_2CH_2$—, and —$CH_2CH_2CH_2$—.

In embodiments of the polymer of the invention where the linking nitrogen atom is not covalently attached to a reactive group, the polymer typically has the following structure:

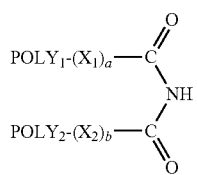
(I)

wherein $POLY_1$, $POLY_2$, (a), (b), $X_1$ (when present), and $X_2$ (when present) are as previously defined.

In embodiments of the polymer of the invention that further comprise a reactive group, the polymer will typically comprise the following structure:

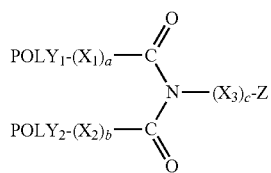
(II)

wherein:

$POLY_1$, $POLY_2$, (a), (b), $X_1$ (when present), and $X_2$ (when present) are as previously defined;

$X^3$, when present, is a third spacer moiety;

(c) is either zero or one; and

Z is a reactive group.

The third spacer moiety, $X_3$, when present, can be any atom or series of atoms connecting one part of a molecule to another. Although the third spacer moiety is typically different from the first and/or second spacer moieties (when present), the third spacer moiety can be the same as another spacer moiety present in the polymer. The third spacer moiety can be selected from one of the group of spacer moieties provided above with respect to first and second spacer moieties. The third spacer moiety is absent when (c) is defined as zero and is present when (c) is defined as one.

A preferred polymer of the invention wherein each of $POLY_1$ and $POLY_2$ is defined as an MPEG has the structure:

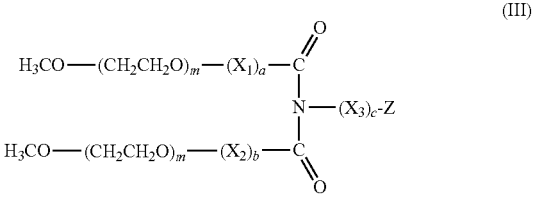
(III)

wherein each (a), (b), (c), $X_1$ (when present), $X_2$ (when present), $X_3$ (when present), and Z are as previously defined, and each m is from 2 to about 4000. PEG versions other than those that are end-capped with methoxy (e.g., end-capped with a hydroxyl or other alkoxy such as benzyloxy) are also envisioned.

In one preferred embodiment of the structure of Formula (III), each of (a) and (b) are defined as zero, resulting in a polymer comprising the following structure:

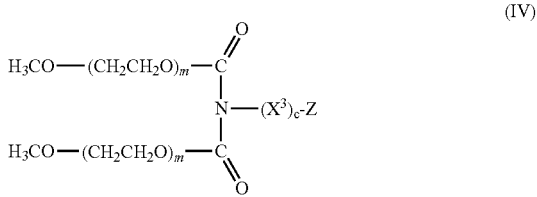
(IV)

wherein each of (m), (c), $X_3$ (when present), and Z are as previously defined. Again, PEGs having end-capping groups other than methoxy can be used.

As noted, the polymer may comprise a reactive moiety designated as "Z" throughout the formulae. Preferred reactive moieties are selected from the group of electrophiles and nucleophiles. Exemplary reactive groups include hydroxyl (—OH), ester, orthoester, carbonate, acetal, aldehyde, aldehyde hydrate, ketone, vinyl ketone, ketone hydrate, thione, thione hydrate, hemiketal, sulfur-substituted hemiketal, ketal, alkenyl, acrylate, methacrylate, acrylamide, sulfone, amine, hydrazide, thiol, disulfide, thiol hydrate, carboxylic acid, isocyanate, isothiocyanate, maleimide

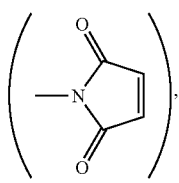

succinimide

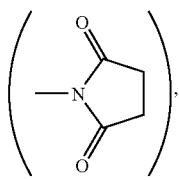

benzotriazole

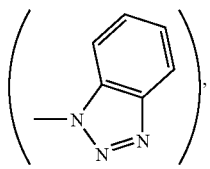

vinylsulfone, chloroethylsulfone, dithiopyridine, vinylpyridine, iodoacetamide, epoxide, glyoxals, diones, mesylates, tosylates, thiosulfonate, tresylate, and silane. Specific examples of preferred reactive groups include amine, carboxylic acid, ester, aldehyde, acetal, succinimide, and maleimide.

Illustrative examples of $X_3$ and Z combinations include

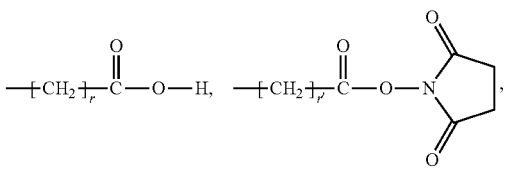

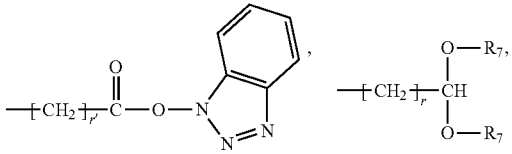

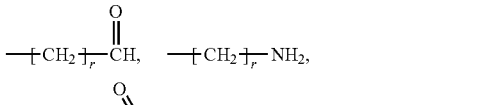

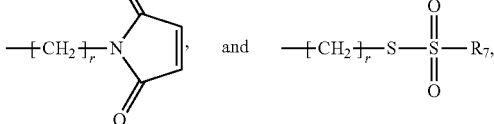

wherein r is 1-5, r' is 0-5, and $R_7$ is aryl or alkyl.

Thus, the polymers of the invention comprise many forms. Exemplary versions of the polymers of the present invention include the following:

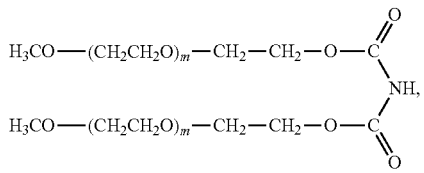
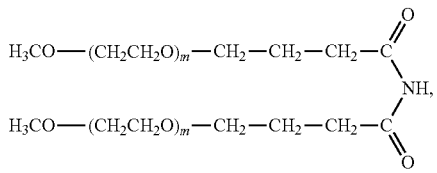

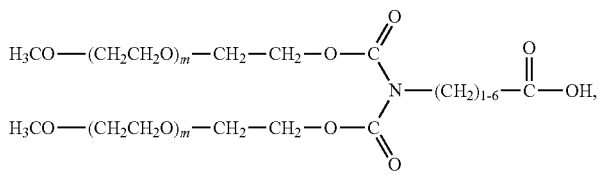

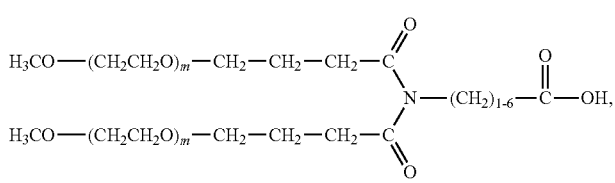

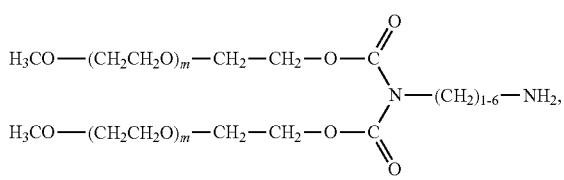
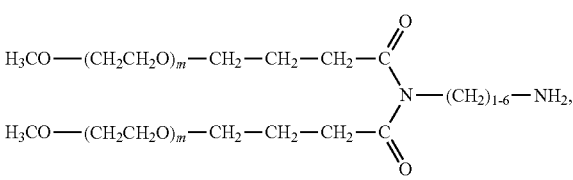

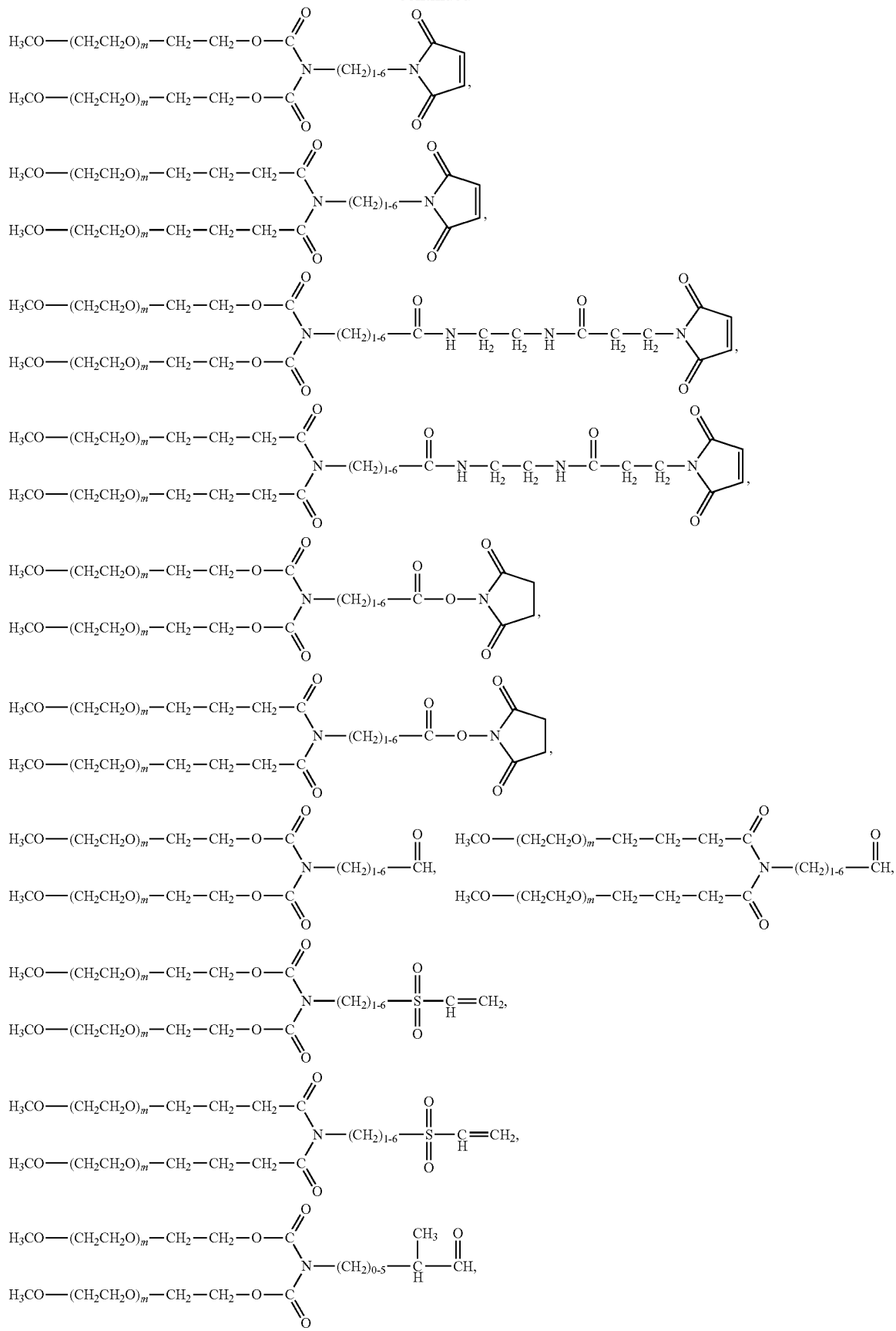

-continued
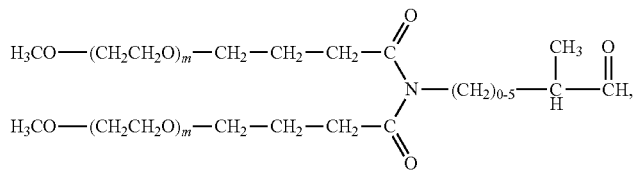
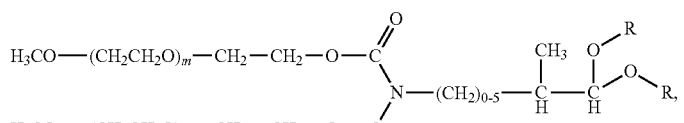
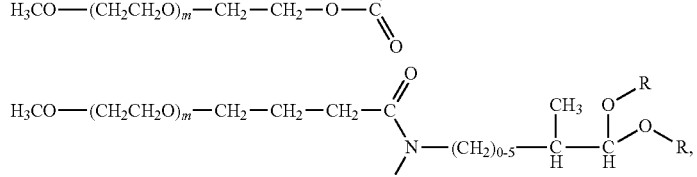
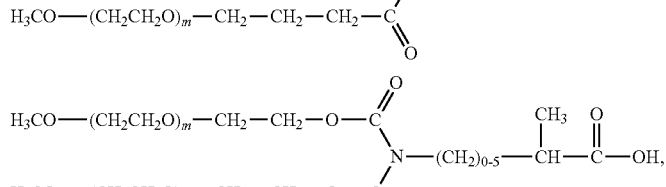
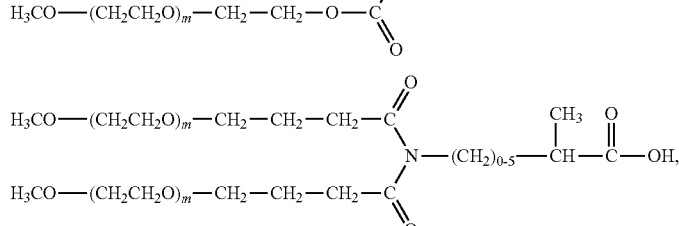
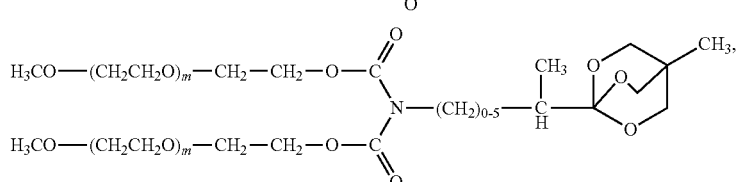
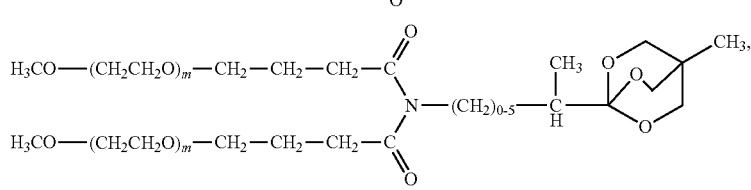
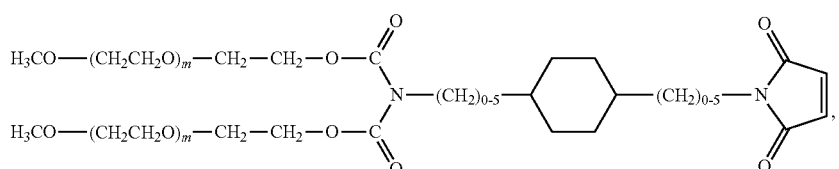
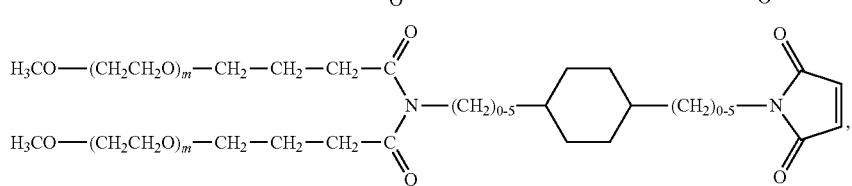

-continued
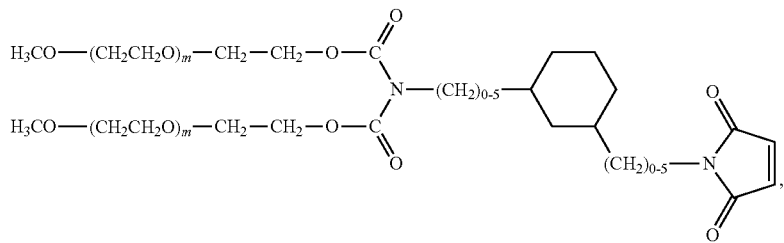
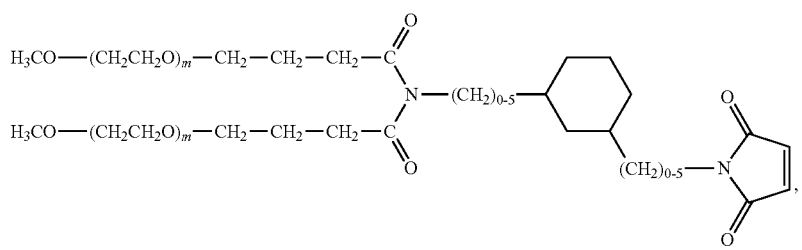
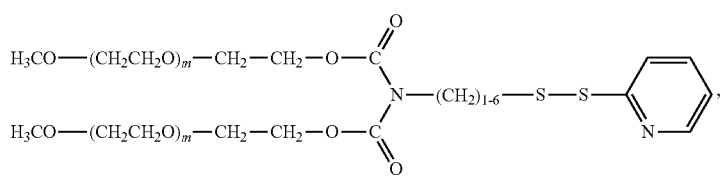
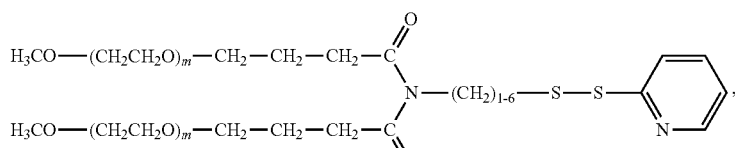
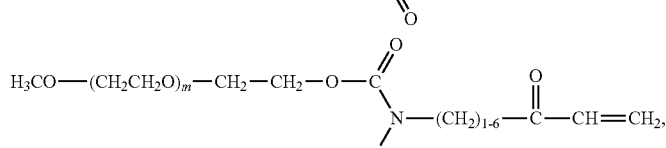
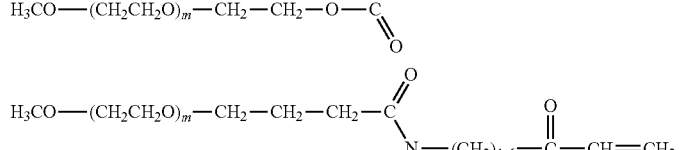
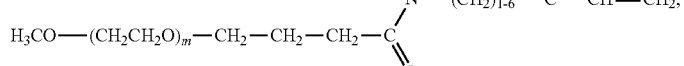
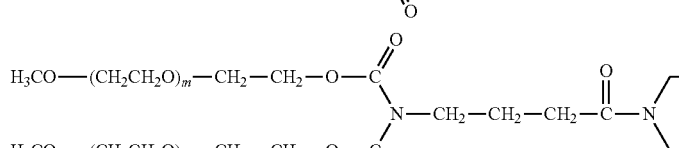
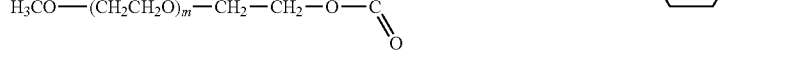
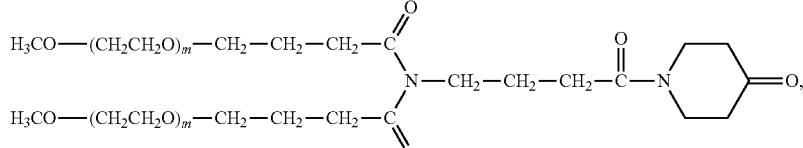
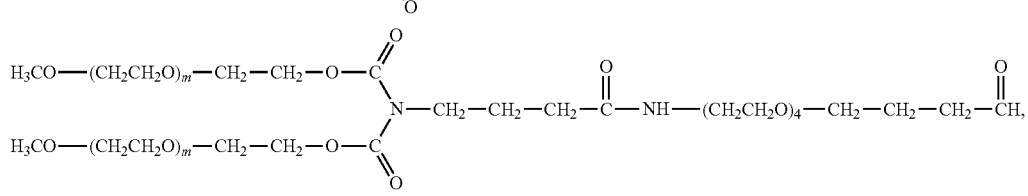

-continued

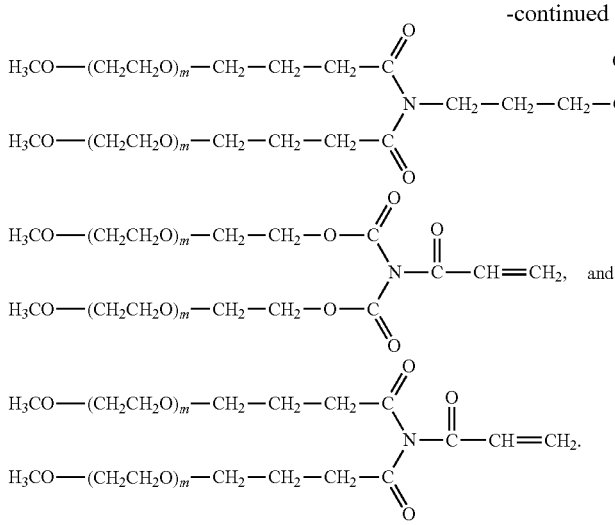

wherein each (m) is as previously defined and R is an organic group, preferably C1-C6 alkyl. Again, PEGs having end-capping groups other than methoxy can be used.

The polymers of the invention can be prepared by one of ordinary skill in the art based upon reading the present disclosure. Further, the polymers of the invention can be prepared in any number of ways. Consequently, the polymers provided herein are not limited to the specific technique or approach used in their preparation. Preferred approaches, however, will be discussed in detail below.

In one approach for providing the polymers of the invention, the two polymer segments are linked to the imide group prior to attachment of a reactive group to the linking nitrogen atom. In this embodiment, the method comprises the steps of (i) providing a first water-soluble polymer segment carrying a first reactive group that comprises a carbonyl group (C=O), (ii) reacting the first water-soluble polymer segment with anhydrous ammonia to form a water-soluble polymer intermediate carrying a terminal —C(O)—NH$_2$ group, (iii) treating the water-soluble polymer intermediate with a strong base to remove a proton from the terminal —C(O)—NH$_2$ group, (iv) reacting the water-soluble polymer intermediate with a second water-soluble polymer segment carrying a second reactive group comprising a carbonyl group to form a water-soluble polymer of the invention. As previously stated, the water-soluble polymer of the invention comprises (i) an imide group comprising a linking nitrogen atom, a first carbonyl group covalently attached to the linking nitrogen atom, and a second carbonyl group covalently attached to the linking nitrogen atom; (ii) a first water-soluble polymer segment covalently attached, either directly or through one or more atoms, to the first carbonyl group of the imide group; and (iii) a second water-soluble polymer segment covalently attached, either directly or through one or more atoms, to the second carbonyl group of the imide group. Optionally, the method further comprises the step of attaching a reactive group to the linking nitrogen atom of the imide-linked water-soluble polymer.

In the method described immediately above, a protected or derivatized form of ammonia optionally can be used in place of anhydrous ammonia. When such a protected or derivatized form of ammonia is used, however, the method further includes performing a deprotecting or de-derivatizing step prior to carrying out any further synthetic steps.

In one embodiment, the first and second carbonyl-containing reactive groups carried by the water-soluble polymer segments, which may be the same or different, are each carbonate-containing reactive groups having the structure —O—C(O)—O—X$_r$, wherein X$_r$ is aryl, substituted aryl, heteroaryl, substituted heteroaryl, heterocycle, or substituted heterocycle. Exemplary X$_r$ moieties include 1-benzotriazolyl, o-, m-, or p-nitrophenyl, and N-succinimidyl.

Preferred water-soluble polymer segments carrying a reactive group that comprises a carbonyl group (C=O) include MPEG terminating in benzotriazole carbonate ("mPEG-BTC"), MPEG terminating in the succinimidyl ester of propionic acid ("mPEG-SPA"), mPEG terminating in the succinimidyl ester of butanoic acid ("mPEG-SBA"), mPEG terminating in a thioester ("mPEG-OPTE"), and mPEG terminating in a double ester ("mPEG-CM-HBA-NHS"). Each of these polymers is available from Nektar Therapeutics (Huntsville, Ala.).

As noted, the method may include the step of attaching a reactive group, which is preferably accomplished by treating the imide-linked water-soluble polymer [from step (iv), above] with a strong base to remove a proton from the linking nitrogen atom and reacting the imide-linked water-soluble polymer with a molecule having the structure Z—(X$_3$)$_c$-Q, wherein Z is a reactive group, (c) is either zero or one, X$_3$, when present, is a spacer moiety, and Q is a leaving group. Note that X, (c), and X$_3$ and correspond to the moieties carrying the same designation in Formulas (II)-(IV) above. Exemplary leaving groups include halo and sulfonate esters. Among halo moieties, bromo, chloro, and iodo are preferred, with bromo and chloro being particularly preferred. With respect to sulfonate esters, methanesulfonate (abbreviated "Ms"), trifluoromethanesulfonate, trichloromethanesulfonate, 2,2,2-trifluoroethanesulfonate, 2,2,2-trichloroethanesulfonate, nonafluorobutanesulfonate, p-bromobenzenesulfonate, p-nitrobenzenesulfonate, and p-toluenesulfonate are particularly preferred, although other sulfonate esters and similarly constituted leaving groups known to those of ordinary skill in the art can be used as well. The presence of the leaving group allows the linking nitrogen atom to react with the molecule in a nucleophilic substitution reaction, resulting in covalent attachment of the Z reactive group (along with the X$_3$ spacer when present) to the imide-linked polymer.

An exemplary reaction scheme utilizing the above-described method is shown below as Reaction Scheme I. As shown, an MPEG molecule carrying a benzotriazolyl carbonate reactive group is reacted with anhydrous ammonia to form a polymer intermediate carrying a terminal —C(O)—NH$_2$ group. A proton is removed from the terminal —C(O)—NH$_2$ group using a strong base and a second polymer segment carrying a benzotriazolyl carbonate reactive group is reacted with the polymer intermediate to form an imide-linked polymer. Following a second treatment with a strong base, a reactive group is attached to the linking nitrogen atom. In this case, the terminal reactive group is an ortho ester that can be readily converted by hydrolysis to the corresponding carboxylic acid. The specific reactive groups and polymer segments used in this reaction scheme could be changed without departing from the invention as explained above.

In another approach for providing polymers of the invention, a reactive group is attached to a first polymer segment prior to attaching the second polymer segment to form the imide-linked polymer.

In this embodiment, the method comprises: (i) providing a first water-soluble polymer segment carrying a first reactive group, the first reactive group comprising a carbonyl group, (ii) reacting the first water-soluble polymer segment with a molecule comprising a second reactive group and an amine group, optionally separated by a spacer moiety, to form a water-soluble polymer intermediate comprising a —C(O)—NH— linkage between the water-soluble polymer segment and the second reactive group, (iii) treating the water-soluble polymer intermediate with a strong base to remove a proton from the nitrogen atom of the —C(O)—NH— linkage, and (iv) reacting the water-soluble polymer intermediate with a second water-soluble polymer segment carrying a third reac-

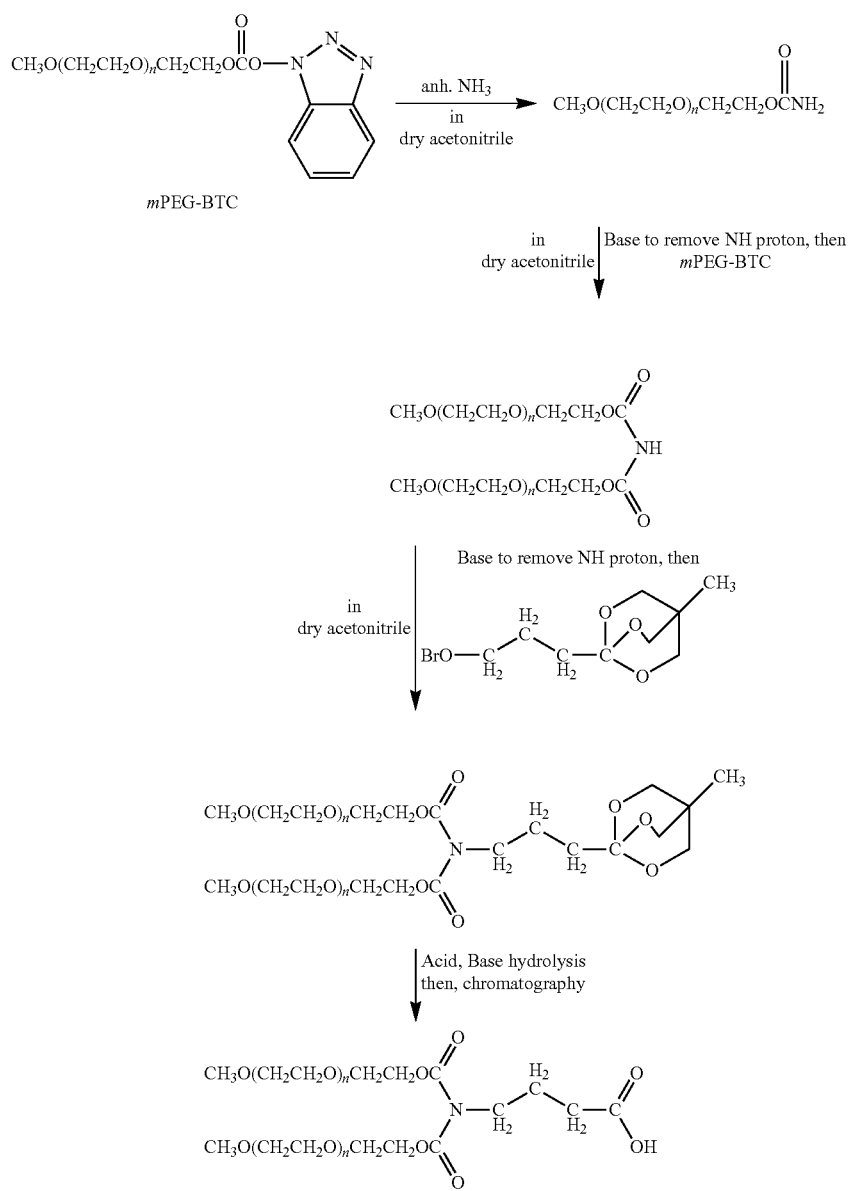

Reaction Scheme I tive group comprising a carbonyl group to form an imide-linked water-soluble polymer, the imide linking group comprising a linking nitrogen atom, a first carbonyl group covalently attached to the linking nitrogen atom, and a second carbonyl group covalently attached to the linking nitrogen atom.

Preferably, the molecule comprising a second reactive group and an amine group has the structure Z—$(X_3)_c$—$NH_2$, wherein Z is the second reactive group, (c) is either zero or one, and $X_3$, when present, is a spacer moiety. Note that X, (c), and $X_3$ and correspond to the moieties carrying the same designation in Formulas (II)-(IV) above.

An exemplary reaction scheme utilizing the above-described method is shown below as Reaction Scheme II. As shown, an MPEG molecule having a terminal benzotriazolyl carbonate group is reacted with a molecule carrying a terminal amine group and a second reactive group, which in this case is an acetal group where R is an organic radical such as alkyl. The resulting polymer is treated with a strong base and reacted with a second benzotriazolyl carbonate terminated mPEG to form an imide-linked polymer carrying an acetal group. The acetal group can then be derivatized as desired, such as by hydrolysis to form the corresponding aldehyde.

ized to include a reactive group (e.g., active ester, thiol, maleimide, aldehyde, ketone, and so forth).

For example, when the polymer bears a carboxylic acid as the reactive group, the corresponding ester can be formed using conventional techniques. For example, the carboxylic acid can undergo acid-catalyzed condensation with an alcohol, thereby providing the corresponding ester. One approach to accomplish this is to use the method commonly referred to as a Fischer esterification reaction. Other techniques for forming a desired ester are known by those of ordinary skill in the art.

In addition, polymers bearing a carboxylic acid can be modified to form useful reactive groups other than esters. For example, the carboxylic acid can be further derivatized to form acyl halides, acyl pseudohalides, such as acyl cyanide, acyl isocyanate, and acyl azide, neutral salts, such as alkali metal or alkaline-earth metal salts (e.g. calcium, sodium, and barium salts), esters, anhydrides, amides, imides, hydrazides, and the like. In a preferred embodiment, the carboxylic acid is esterified to form an N-succinimidyl ester, o-, m-, or p-nitrophenyl ester, 1-benzotriazolyl ester, imidazolyl ester, or N-sulfosuccinimidyl ester. For example, the carboxylic acid can be converted into the corresponding N-succinimidyl ester

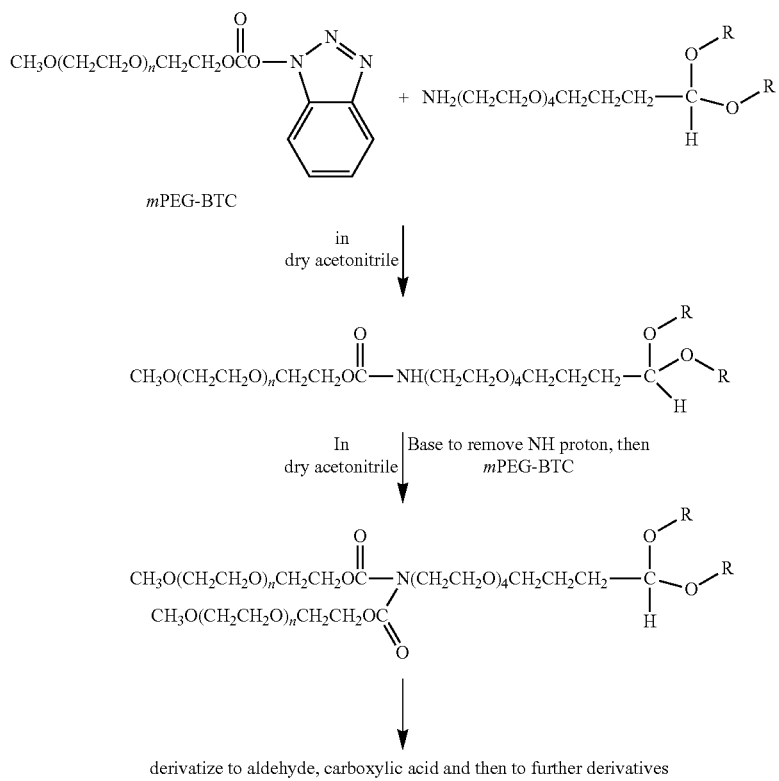

The strong base used in the methods described above can be any strong base known in the art. Preferably, the base is an alkali metal hydroxide or alkali metal hydride (e.g., NaOH or NaH).

For any given polymer, the methods described above advantageously provide the ability to further transform the polymer (either prior or subsequent to any deprotection step) so that it bears a specific reactive group. Thus, using techniques well known in the art, the polymer can be functionalby reacting the carboxylic acid with dicyclohexyl carbodiimide (DCC) or diisopropyl carbodiimide (DIC) in the presence of a N-hydroxysuccinimide.

The steps of the synthesis methods described above take place in an appropriate solvent. One of ordinary skill in the art can determine whether any specific solvent is appropriate for any given reaction. Typically, however, the solvent is a nonpolar solvent or a polar aprotic solvent. Nonlimiting examples of nonpolar solvents include benzene, xylene, dioxane, tetrahydrofuran (THF), and toluene. Exemplary polar aprotic solvents include, but are not limited to, acetonitrile, DMSO (dimethyl sulfoxide), HMPA (hexamethylphosphoramide), DMF (dimethylformamide), DMA (dimethylacetamide), and NMP (N-methylpyrrolidinone).

The method of preparing the polymers optionally comprises an additional step of isolating and recovering the polymer once it is formed. Known methods can be used to isolate the polymer, but it is particularly preferred to use chromatography, e.g., size exclusion chromatography. Alternately or in addition, the method includes the step of purifying the polymer once it is formed. Again, standard art-known purification methods can be used to purify the polymer.

The polymers of the invention can be stored under an inert atmosphere, such as under argon or under nitrogen. In this way, potentially degradative processes associated with, for example, atmospheric oxygen, are reduced or avoided entirely. In some cases, to avoid oxidative degradation, antioxidants, such as butylated hydroxyl toluene (BHT), can be added to the final product prior to storage. In addition, it is preferred to minimize the amount of moisture associated with the storage conditions to reduce potentially damaging reactions associated with water. Moreover, it is preferred to keep the storage conditions dark in order to prevent certain degradative processes that involve light. Thus, preferred storage conditions include one or more of the following: storage under dry argon or another dry inert gas; storage at temperatures below about −15° C.; storage in the absence of light; and storage with a suitable amount (e.g., about 50 to about 500 parts per million) of an antioxidant such as BHT.

The above-described polymers are useful for conjugation to biologically active agents or surfaces comprising at least one group suitable for reaction with the reactive group on the polymer. For example, amino groups (e.g., primary amines), hydrazines, hydrazides, and alcohols on an active agent or surface will react with a carboxylic acid group on the polymer. In addition, a more "activated" version of the carboxylic acid of the polymer can be prepared in order to enhance reactivity to the biologically active agent or surface. Methods for activating carboxylic acids are known in the art and include, for example, the method for forming an active ester described above. Other approaches for activating a carboxylic acid are known to those of ordinary skill in the art.

A conjugate of the invention comprises: (i) an imide group comprising a linking nitrogen atom, a first carbonyl group covalently attached to the linking nitrogen atom, and a second carbonyl group covalently attached to the linking nitrogen atom; (ii) a first water-soluble polymer segment covalently attached, either directly or through one or more atoms, to the first carbonyl group of the imide group; (iii) a second water-soluble polymer segment covalently attached, either directly or through one or more atoms, to the second carbonyl group of the imide group; and (iv) a pharmacologically active agent covalently attached, either directly or through one or more atoms, to the linking nitrogen atom.

In one embodiment, the conjugate of the invention has the structure:

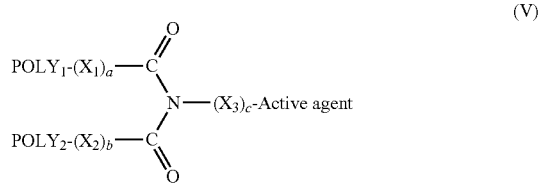

(V)

wherein $POLY_1$, $POLY_2$, (a), (b), (c), $X_1$ (when present), $X_2$ (when present), and $X_3$ (when present) are as defined above, and "Active agent" represents a residue of a pharmacologically active agent.

Typically, the polymer is added to the active agent or surface at an equimolar amount (with respect to the desired number of groups suitable for reaction with the reactive group) or at a molar excess. For example, the polymer can be added to the target active agent at a molar ratio of about 1:1 (polymer:active agent), 1.5:1, 2:1, 3:1, 4:1, 5:1, 6:1, 8:1, or 10:1. The conjugation reaction is allowed to proceed until substantially no further conjugation occurs, which can generally be determined by monitoring the progress of the reaction over time. Progress of the reaction can be monitored by withdrawing aliquots from the reaction mixture at various time points and analyzing the reaction mixture by SDS-PAGE or MALDI-TOF mass spectrometry or any other suitable analytical method. Once a plateau is reached with respect to the amount of conjugate formed or the amount of unconjugated polymer remaining, the reaction is assumed to be complete. Typically, the conjugation reaction takes anywhere from minutes to several hours (e.g., from 5 minutes to 24 hours or more). The resulting product mixture is preferably, but not necessarily, purified to separate out excess reagents, unconjugated reactants (e.g., active agent), undesired multi-conjugated species, and free or unreacted polymer. The resulting conjugates can then be further characterized using analytical methods such as MALDI, capillary electrophoresis, gel electrophoresis, and/or chromatography.

With respect to polymer-active agent conjugates, the conjugates can be purified to obtain/isolate different conjugated species. Alternatively, and more preferably for lower molecular weight (e.g., less than about 20 kiloDaltons, more preferably less than about 10 kiloDaltons) polymers, the product mixture can be purified to obtain the distribution of water-soluble polymer segments per active agent. For example, the product mixture can be purified to obtain an average of anywhere from one to five PEGs per active agent (e.g., protein), typically an average of about three PEGs per active agent (e.g., protein). The strategy for purification of the final conjugate reaction mixture will depend upon a number of factors, including, for example, the molecular weight of the polymer employed, the particular active agent, the desired dosing regimen, and the residual activity and in vivo properties of the individual conjugate(s).

If desired, conjugates having different molecular weights can be isolated using gel filtration chromatography. That is to say, gel filtration chromatography is used to fractionate differently numbered polymer-to-active agent ratios (e.g., 1-mer, 2-mer, 3-mer, and so forth, wherein "1-mer" indicates 1 polymer to active agent, "2-mer" indicates two polymers to active agent, and so on) on the basis of their differing molecular weights (where the difference corresponds essentially to the average molecular weight of the water-soluble polymer segments). For example, in an exemplary reaction where a 100 kDa protein is randomly conjugated to a PEG alkanoic acid having a molecular weight of about 20 kDa, the resulting reaction mixture will likely contain unmodified protein (MW 100 kDa), mono-pegylated protein (MW 120 kDa), di-pegylated protein (MW 140 kDa), and so forth. While this approach can be used to separate PEG and other polymer conjugates having different molecular weights, this approach is generally ineffective for separating positional isomers having different polymer attachment sites within the protein. For example, gel filtration chromatography can be used to separate mixtures of PEG 1-mers, 2-mers, 3-mers, and so forth, although each of the recovered PEG-mer compositions may contain PEGs attached to different reactive amino groups (e.g., lysine residues) within the active agent.

Gel filtration columns suitable for carrying out this type of separation include Superdex™ and Sephadex™ columns available from Amersham Biosciences (Piscataway, N.J.). Selection of a particular column will depend upon the desired fractionation range desired. Elution is generally carried out using a suitable buffer, such as phosphate, acetate, or the like. The collected fractions may be analyzed by a number of different methods, for example, (i) optical density (OD) at 280 nm for protein content, (ii) bovine serum albumin (BSA) protein analysis, (iii) iodine testing for PEG content [Sims et al. (1980) Anal. Biochem, 107:60-63], and (iv) sodium dodecyl sulfphate polyacrylamide gel electrophoresis (SDS PAGE), followed by staining with barium iodide.

Separation of positional isomers is carried out by reverse phase chromatography using a reverse phase-high performance liquid chromatography (RP-HPLC) C18 column (Amersham Biosciences or Vydac) or by ion exchange chromatography using an ion exchange column, e.g., a Sepharose™ ion exchange column available from Amersham Biosciences. Either approach can be used to separate polymer-active agent isomers having the same molecular weight (positional isomers).

Following conjugation, and optionally additional separation steps, the conjugate mixture can be concentrated, sterile filtered, and stored at low a temperature, typically from about −20° C. to about −80° C. Alternatively, the conjugate may be lyophilized, either with or without residual buffer and stored as a lyophilized powder. In some instances, it is preferable to exchange a buffer used for conjugation, such as sodium acetate, for a volatile buffer such as ammonium carbonate or ammonium acetate, that can be readily removed during lyophilization, so that the lyophilized powder is absent residual buffer. Alternatively, a buffer exchange step may be used using a formulation buffer, so that the lyophilized conjugate is in a form suitable for reconstitution into a formulation buffer and ultimately for administration to a mammal.

The polymers of the invention can be attached, either covalently or noncovalently, to a number of entities including films, chemical separation and purification surfaces, solid supports, metal surfaces such as gold, titanium, tantalum, niobium, aluminum, steel, and their oxides, silicon oxide, macromolecules (e.g., proteins, polypeptides, and so forth), and small molecules. Additionally, the polymers can also be used in biochemical sensors, bioelectronic switches, and gates. The polymers can also be employed as carriers for peptide synthesis, for the preparation of polymer-coated surfaces and polymer grafts, to prepare polymer-ligand conjugates for affinity partitioning, to prepare cross-linked or non-cross-linked hydrogels, and to prepare polymer-cofactor adducts for bioreactors.

A biologically active agent for use in coupling to a polymer as presented herein may be any one or more of the following. Suitable agents can be selected from, for example, hypnotics and sedatives, psychic energizers, tranquilizers, respiratory drugs, anticonvulsants, muscle relaxants, antiparkinson agents (dopamine antagnonists), analgesics, anti-inflammatories, antianxiety drugs (anxiolytics), appetite suppressants, antimigraine agents, muscle contractants, anti-infectives (antibiotics, antivirals, antifungals, vaccines) antiarthritics, antimalarials, antiemetics, anepileptics, bronchodilators, cytokines, growth factors, anti-cancer agents, antithrombotic agents, antihypertensives, cardiovascular drugs, antiarrhythimics, antioxicants, anti-asthma agents, hormonal agents including contraceptives, sympathomimetics, diuretics, lipid regulating agents, antiandrogenic agents, antiparasitics, anticoagulants, neoplastics, antineoplastics, hypoglycemics, nutritional agents and supplements, growth supplements, antienteritis agents, vaccines, antibodies, diagnostic agents, and contrasting agents.

More particularly, the active agent may fall into one of a number of structural classes, including but not limited to small molecules (preferably water insoluble small molecules), peptides, polypeptides, proteins, polysaccharides, steroids, nucleotides, oligonucleotides, polynucleotides, fats, electrolytes, and the like. Preferably, an active agent for coupling to a polymer as described herein possesses a native amino group, or alternatively, is modified to contain at least one reactive amino group suitable for conjugating to a polymer described herein.

Specific examples of active agents suitable for covalent attachment include, but are not limited to, aspariginase, amdoxovir (DAPD), antide, becaplermin, calcitonins, cyanovirin, denileukin diftitox, erythropoietin (EPO), EPO agonists (e.g., peptides from about 10-40 amino acids in length and comprising a particular core sequence as described in WO 96/40749), dornase alpha, erythropoiesis stimulating protein (NESP), coagulation factors such as Factor V, Factor VII, Factor VIIa, Factor VIII, Factor IX, Factor X, Factor XII, Factor XIII, von Willebrand factor; ceredase, cerezyme, alpha-glucosidase, collagen, cyclosporin, alpha defensins, beta defensins, exedin-4, granulocyte colony stimulating factor (GCSF), thrombopoietin (TPO), alpha-1 proteinase inhibitor, elcatonin, granulocyte macrophage colony stimulating factor (GMCSF), fibrinogen, filgrastim, growth hormones human growth hormone (hGH), growth hormone releasing hormone (GHRH), GRO-beta, GRO-beta antibody, bone morphogenic proteins such as bone morphogenic protein-2, bone morphogenic protein-6, OP-1; acidic fibroblast growth factor, basic fibroblast growth factor, CD-40 ligand, heparin, human serum albumin, low molecular weight heparin (LMWH), interferons such as interferon alpha, interferon beta, interferon gamma, interferon omega, interferon tau, consensus interferon; interleukins and interleukin receptors such as interleukin-1 receptor, interleukin-2, interluekin-2 fusion proteins, interleukin-1 receptor antagonist, interleukin-3, interleukin-4, interleukin-4 receptor, interleukin-6, interleukin-8, interleukin-12, interleukin-13 receptor, interleukin-17 receptor; lactoferrin and lactoferrin fragments, luteinizing hormone releasing hormone (FSH), insulin, proinsulin, insulin analogues (e.g., mono-acylated insulin as described in U.S. Pat. No. 5,922,675), amylin, C-peptide, somatostatin, somatostatin analogs including octreotide, vasopressin, follicle stimulating hormone (FSH), influenza vaccine, insulin-like growth factor (IGF), insulintropin, macrophage colony stimulating factor (M-CSF), plasminogen activators such as alteplase, urokinase, reteplase, streptokinase, pamiteplase, lanoteplase, and teneteplase; nerve growth factor (NGF), osteoprotegerin, platelet-derived growth factor, tissue growth factors, transforming growth factor-1, vascular endothelial growth factor, leukemia inhibiting factor, keratinocyte growth factor (KGF), glial growth factor (GGF), T Cell receptors, CD molecules/antigens, tumor necrosis factor (TNF), monocyte chemoattractant protein-1, endothelial growth factors, parathyroid hormone (PTH), glucagon-like peptide, somatotropin, thymosin alpha 1, rasburicase, thymosin alpha 1 IIb/IIIa inhibitor, thymosin beta 10, thymosin beta 9, thymosin beta 4, alpha-1 antitrypsin, phosphodiesterase (PDE) compounds, VLA-4 (very late antigen-4), VLA-4 inhibitors, bisphosphonates, respiratory syncytial virus antibody, cystic fibrosis transmembrane regulator (CFTR) gene, deoxyribonuclease (Dnase), bactericidal/permeability increasing protein (BPI), and anti-CMV antibody.

Exemplary monoclonal antibodies include etanercept (a dimeric fusion protein consisting of the extracellular ligand-binding portion of the human 75 kD TNF receptor linked to the Fc portion of IgG1), abciximab, adalimumab, afelimomab, alemtuzumab, antibody to B-lymphocyte (lymphostat-B™), atlizumab, basiliximab, bevacizumab, biciromab, CAT-213 or bertilimumab, CDP-571, CDP-870, cetuximab, clenoliximab, daclizumab, eculizumab, edrecolomab, efalizumab, epratuzumab, fontolizumab, gavilimomab, gemtuzumab ozogamicin, ibritumomab tiuxetan, infliximab, inolimomab, keliximab, labetuzumab, lerdelimumab, radiolabeled lym-1, metelimumab, mepolizumab, mitumomab, muromonad-CD3, nebacumab, natalizumab, odulimomab, omalizumab, oregovbmab, palivizumab, pemtumomab, pexelizumab, rituximab satumomab pendetide, sevirumab, siplizumab, tositumomab and $I^{131}$ tositumomab, olizumab, trastuzumab, tuvirumab, and visilizumab.

Additional agents suitable for covalent attachment include, but are not limited to, adefovir, alosetron, amifostine, amiodarone, aminocaproic acid, aminohippurate sodium, aminoglutethimide, aminolevulinic acid, aminosalicylic acid, amsacrine, anagrelide, anastrozole, aripiprazole, asparaginase, anthracyclines, bexarotene, bicalutamide, bleomycin, buserelin, busulfan, cabergoline, capecitabine, carboplatin, carmustine, chlorambucin, cilastatin sodium, cisplatin, cladribine, clodronate, cyclophosphamide, cyproterone, cytarabine, camptothecins, 13-cis retinoic acid, all trans retinoic acid; dacarbazine, dactinomycin, daunorubicin, deferoxamine, dexamethasone, diclofenac, diethylstilbestrol, docetaxel, doxorubicin, dutasteride, epirubicin, estramustine, etoposide, exemestane, ezetimibe, fexofenadine, fludarabine, fludrocortisone, fluorouracil, fluoxymesterone, flutamide, fondaparinux, fulvestrant, gamma-hydroxybutyrate, gemcitabine, epinephrine, L-Dopa, hydroxyurea, idarubicin, ifosfamide, imatinib, irinotecan, itraconazole, goserelin, letrozole, leucovorin, levamisole, lisinopril, lovothyroxine sodium, lomustine, mechlorethamine, medroxyprogesterone, megestrol, melphalan, mercaptopurine, metaraminol bitartrate, methotrexate, metoclopramide, mexiletine, mitomycin, mitotane, mitoxantrone, naloxone, nicotine, nilutamide, nitisinone, octreotide, oxaliplatin, pamidronate, pentostatin, pilcamycin, porfimer, prednisone, procarbazine, prochlorperazine, ondansetron, oxaliplatin, raltitrexed, sirolimus, streptozocin, tacrolimus, pimecrolimus, tamoxifen, tegaserod, temozolomide, teniposide, testosterone, tetrahydrocannabinol, thalidomide, thioguanine, thiotepa, topotecan, treprostinil, tretinoin, valdecoxib, celecoxib, rofecoxib, valrubicin, vinblastine, vincristine, vindesine, vinorelbine, voriconazole, dolasetron, granisetron; formoterol, fluticasone, leuprolide, midazolam, alprazolam, amphotericin B, podophylotoxins, nucleoside antivirals, aroyl hydrazones, sumatriptan; macrolides such as erythromycin, oleandomycin, troleandomycin, roxithromycin, clarithromycin, davercin, azithromycin, flurithromycin, dirithromycin, josamycin, spiromycin, midecamycin, loratadine, desloratadine, leucomycin, miocamycin, rokitamycin, andazithromycin, and swinolide A; fluoroquinolones such as ciprofloxacin, ofloxacin, levofloxacin, trovafloxacin, alatrofloxacin, moxifloxicin, norfloxacin, enoxacin, grepafloxacin, gatifloxacin, lomefloxacin, sparfloxacin, temafloxacin, pefloxacin, amifloxacin, fleroxacin, tosufloxacin, prulifloxacin, irloxacin, pazufloxacin, clinafloxacin, and sitafloxacin; aminoglycosides such as gentamicin, netilmicin, paramecin, tobramycin, amikacin, kanamycin, neomycin, and streptomycin, vancomycin, teicoplanin, rampolanin, mideplanin, colistin, daptomycin, gramicidin, colistimethate; polymixins such as polymixin B, capreomycin, bacitracin, penems; penicillins including penicllinase-sensitive agents like penicillin G, penicillin V; penicllinase-resistant agents like methicillin, oxacillin, cloxacillin, dicloxacillin, floxacillin, nafcillin; gram negative microorganism active agents like ampicillin, amoxicillin, and hetacillin, cillin, and galampicillin; antipseudomonal penicillins like carbenicillin, ticarcillin, azlocillin, mezlocillin, and piperacillin; cephalosporins like cefpodoxime, cefprozil, ceftbuten, ceftizoxime, ceftriaxone, cephalothin, cephapirin, cephalexin, cephradrine, cefoxitin, cefamandole, cefazolin, cephaloridine, cefaclor, cefadroxil, cephaloglycin, cefuroxime, ceforanide, cefotaxime, cefatrizine, cephacetrile, cefepime, cefixime, cefonicid, cefoperazone, cefotetan, cefmetazole, ceftazidime, loracarbef, and moxalactam, monobactams like aztreonam; and carbapenems such as imipenem, meropenem, and ertapenem, pentamidine isetionate, albuterol sulfate, lidocaine, metaproterenol sulfate, beclomethasone diprepionate, triamcinolone acetamide, budesonide acetonide, fluticasone, ipratropium bromide, flunisolide, cromolyn sodium, and ergotamine tartrate; taxanes such as paclitaxel; SN-38, and tyrphostines.

Preferred small molecules for coupling to a polymer as described herein are those having at least one naturally occurring amino group. Preferred molecules such as these include aminohippurate sodium, amphotericin B, doxorubicin, aminocaproic acid, aminolevulinic acid, aminosalicylic acid, metaraminol bitartrate, pamidronate disodium, daunorubicin, levothyroxine sodium, lisinopril, cilastatin sodium, mexiletine, cephalexin, deferoxamine, and amifostine.

Preferred peptides or proteins for coupling to a polymer as described herein include EPO, IFN-α, IFN-β, consensus IFN, Factor VIII, Factor IX, GCSF, GMCSF, hGH, insulin, FSH, and PTH.

The above exemplary biologically active agents are meant to encompass, where applicable, analogues, agonists, antagonists, inhibitors, isomers, and pharmaceutically acceptable salt forms thereof. In reference to peptides and proteins, the invention is intended to encompass synthetic, recombinant, native, glycosylated, and non-glycosylated forms, as well as biologically active fragments thereof.

The present invention also includes pharmaceutical preparations comprising a conjugate as provided herein in combination with a pharmaceutical excipient. Generally, the conjugate itself will be in a solid form (e.g., a precipitate), which can be combined with a suitable pharmaceutical excipient that can be in either solid or liquid form. In one embodiment, the conjugate is formulated with a liquid diluent, such as bacteriostatic water for injection, dextrose 5% in water, phosphate-buffered saline, Ringer's solution, saline solution, sterile water, deionized water, or combinations thereof.

Exemplary excipients include, without limitation, those selected from the group consisting of carbohydrates, inorganic salts, antimicrobial agents, antioxidants, surfactants, buffers, acids, bases, and combinations thereof.

A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like.

The excipient can also include an inorganic salt or buffer such as citric acid, sodium chloride, potassium chloride, sodium sulfate, potassium nitrate, sodium phosphate monobasic, sodium phosphate dibasic, and combinations thereof.

The preparation may also include an antimicrobial agent for preventing or deterring microbial growth. Nonlimiting examples of antimicrobial agents suitable for the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

An antioxidant can be present in the preparation as well. Antioxidants are used to prevent oxidation, thereby preventing the deterioration of the conjugate or other components of the preparation. Suitable antioxidants for use in the present invention include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

A surfactant may be present as an excipient. Exemplary surfactants include: polysorbates, such as "Tween 20" and "Tween 80," and pluronics such as F68 and F88 (both of which are available from BASF, Mount Olive, N.J.); sorbitan esters; lipids, such as phospholipids such as lecithin and other phosphatidylcholines, phosphatidylethanolamines (although preferably not in liposomal form), fatty acids and fatty esters; steroids, such as cholesterol; and chelating agents, such as EDTA, zinc and other such suitable cations.

Acids or bases may be present as an excipient in the preparation. Nonlimiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The pharmaceutical preparations encompass all types of formulations and in particular those that are suited for injection, e.g., powders that can be reconstituted as well as suspensions and solutions. For example, the pharmaceutical preparation can be in the form of a lyophilized cake or powder. The amount of the conjugate (i.e., the conjugate formed between the active agent and the polymer described herein) in the composition will vary depending on a number of factors, but will optimally be a therapeutically effective dose when the composition is stored in a unit dose container (e.g., a vial). In addition, the pharmaceutical preparation can be housed in a syringe. A therapeutically effective dose can be determined experimentally by repeated administration of increasing amounts of the conjugate in order to determine which amount produces a clinically desired endpoint.

The amount of any individual excipient in the composition will vary depending on the activity of the excipient and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects.

Generally, however, the excipient will be present in the composition in an amount of about 1% to about 99% by weight, preferably from about 5%-98% by weight, more preferably from about 15-95% by weight of the excipient, with concentrations less than 30% by weight most preferred.

These foregoing pharmaceutical excipients along with other excipients are described in "Remington: The Science & Practice of Pharmacy", $19^{th}$ ed., Williams & Williams, (1995), the "Physician's Desk Reference", $52^{nd}$ ed., Medical Economics, Montvale, N.J. (1998), and Kibbe, A. H., Handbook of Pharmaceutical Excipients, $3^{rd}$ Edition, American Pharmaceutical Association, Washington, D.C., 2000.

The pharmaceutical preparations of the present invention are typically, although not necessarily, administered via injection and are therefore generally liquid solutions or suspensions immediately prior to administration. The pharmaceutical preparation can also take other forms such as syrups, creams, ointments, tablets, powders, and the like. Other modes of administration are also included, such as pulmonary, rectal, transdermal, transmucosal, oral, intrathecal, subcutaneous, intra-arterial, and so forth.

As previously described, the conjugates can be administered injected parenterally by intravenous injection, or less preferably by intramuscular or by subcutaneous injection. Suitable formulation types for parenteral administration include ready-for-injection solutions, dry powders for combination with a solvent prior to use, suspensions ready for injection, dry insoluble compositions for combination with a vehicle prior to use, and emulsions and liquid concentrates for dilution prior to administration, among others.

The invention also provides a method for administering a conjugate as provided herein to a patient suffering from a condition that is responsive to treatment with conjugate. The method comprises administering, generally via injection, a therapeutically effective amount of the conjugate (preferably provided as part of a pharmaceutical preparation). The method of administering may be used to treat any condition that can be remedied or prevented by administration of the particular conjugate. Those of ordinary skill in the art appreciate which conditions a specific conjugate can effectively treat. The actual dose to be administered will vary depend upon the age, weight, and general condition of the subject as well as the severity of the condition being treated, the judgment of the health care professional, and conjugate being administered. Therapeutically effective amounts are known to those skilled in the art and/or are described in the pertinent reference texts and literature. Generally, a therapeutically effective amount will range from about 0.001 mg to 100 mg, preferably in doses from 0.01 mg/day to 75 mg/day, and more preferably in doses from 0.10 mg/day to 50 mg/day.

The unit dosage of any given conjugate (again, preferably provided as part of a pharmaceutical preparation) can be administered in a variety of dosing schedules depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, three times weekly, twice weekly, once weekly, twice monthly, once monthly, and any combination thereof. Once the clinical endpoint has been achieved, dosing of the composition is halted.

One advantage of administering the conjugates of the present invention is that individual water-soluble polymer portions can be cleaved off. Such a result is advantageous when clearance from the body is potentially a problem because of the polymer size. Optimally, cleavage of each water-soluble polymer portion is facilitated through the use of physiologically cleavable and/or enzymatically degradable linkages such as carbonate or ester-containing linkages. In this way, clearance of the conjugate (via cleavage of individual water-soluble polymer portions) can be modulated by selecting the polymer molecular size and the type functional group that would provide the desired clearance properties. One of ordinary skill in the art can determine the proper molecular size of the polymer as well as the cleavable functional group. For example, one of ordinary skill in the art, using routine experimentation, can determine a proper molecular size and cleavable functional group by first preparing a variety of polymer derivatives with different polymer weights and cleavable functional groups, and then obtaining the clearance profile (e.g., through periodic blood or urine sampling) by administering the polymer derivative to a patient and taking periodic blood and/or urine sampling. Once a series of clearance profiles have been obtained for each tested conjugate, a suitable conjugate can be identified.

It is to be understood that while the invention has been described in conjunction with the preferred specific embodiments thereof, that the foregoing description as well as the experimental that follow are intended to illustrate and not limit the scope of the invention. Other aspects, advantages and modifications within the scope of the invention will be apparent to those skilled in the art to which the invention pertains.

All articles, books, patents, patent publications and other publications referenced herein are hereby incorporated by reference in their entireties.

What is claimed is:

1. A water-soluble polymer of Formula Ib:

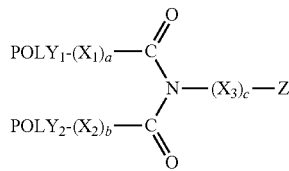

Formula Ib wherein:
POLY$_1$ is a first poly(ethylene glycol) segment;
POLY$_2$ is a second poly(ethylene glycol) segment;
each of (a) and (b) are independently either zero or one;
(c) is one;
X$_1$, when present, is a first spacer moiety;
X$_2$, when present, is a second spacer moiety;
X$_3$ is a third spacer moiety selected from a C1-C10 alkylene group; and
Z is a reactive group.

2. The water-soluble polymer of claim 1, wherein each poly(ethylene glycol) is terminally capped with an end-capping moiety.

3. The water-soluble polymer of claim 2, wherein each end-capping moiety is independently selected from the group consisting of alkoxy, substituted alkoxy, alkenyloxy, substituted alkenyloxy, alkynyloxy, substituted alkynyloxy, aryloxy, substituted aryloxy, and hydroxy.

4. The water-soluble polymer of claim 3, wherein each end-capping moiety is alkoxy.

5. The water-soluble polymer of claim 4, wherein each alkoxy is methoxy.

6. The water-soluble polymer of claim 3, wherein each end-capping moiety is hydroxy.

7. The water-soluble polymer of claim 1, wherein each poly(ethylene glycol) has a weight average molecular weight of from about 100 Daltons to about 100,000 Daltons.

8. The water-soluble polymer of claim 7, wherein each poly(ethylene glycol) has a weight average molecular weight of from about 1,000 Daltons to about 50,000 Daltons.

9. The water-soluble polymer of claim 8, wherein each poly(ethylene glycol) has a weight average molecular weight of from about 5,000 Daltons to about 20,000 Daltons.

10. The water-soluble polymer of claim 1, wherein each of (a) and (b) is one.

11. The water-soluble polymer of claim 10, wherein each of X$_1$ and X$_2$ is the same.

12. The water-soluble polymer of claim 10, wherein each of X$_1$ and X$_2$ is different.

13. The water-soluble polymer of claim 10, wherein:
X$_1$ and X$_2$ are independently selected from the group consisting of: a bivalent cycloalkenyl group comprising 3 to about 20 carbon atoms; an amino acid; a C1-C10 alkylene group; —(CH$_2$)$_o$—Y—(CH$_2$)$_p$—; —C(O)—; —C(S)—; —C(O)—O—; —C(O)—NH—; —NH—C(O)—NH—; —O—C(O)—NH—; and combinations thereof;
(o) and (p) are each independently integers from zero to about 10;
Y is —O—, —S—, or N(R$_6$)—;
R$_6$ is H, alkyl, substituted alkyl, alkenyl, substituted alkenyl, alkynyl, substituted alkynyl, aryl, or substituted aryl; and
X$_1$ or X$_2$ may optionally further include an ethylene oxide oligomer chain comprising 1 to 20 ethylene oxide monomer units.

14. The water-soluble polymer of claim 10, wherein each of X$_1$ and X$_2$ is independently selected from the group consisting of —C(O)—, —C(O)—NH—, —NH—C(O)—NH—, —O—C(O)—NH—, —C(S)—, —CH$_2$—, —CH$_2$—CH$_2$—, —CH$_2$—CH$_2$—CH$_2$—, —CH$_2$—CH$_2$—CH$_2$—CH$_2$—, —O—CH$_2$—, —CH$_2$—O—, —O—CH$_2$—CH$_2$—, —CH$_2$—O—CH$_2$—, —CH$_2$—CH$_2$—O—, —O—CH$_2$—CH$_2$—CH$_2$—, —CH$_2$—O—CH$_2$—CH$_2$—, —CH$_2$—CH$_2$—O—CH$_2$—, —CH$_2$—CH$_2$—CH$_2$—O—, —O—CH$_2$—CH$_2$—CH$_2$—CH$_2$—, —CH$_2$—O—CH$_2$—CH$_2$—CH$_2$—, —CH$_2$—CH$_2$—O—CH$_2$—CH$_2$—, —CH$_2$—CH$_2$—CH$_2$—O—CH$_2$—, —CH$_2$—CH$_2$—CH$_2$—CH$_2$—O—, —C(O)—NH—CH$_2$—, —C(O)—NH—CH$_2$—CH$_2$—, —CH$_2$—C(O)—NH—CH$_2$—, —CH$_2$—CH$_2$—C(O)—NH—, —C(O)—NH—CH$_2$—CH$_2$—CH$_2$—, —CH$_2$—C(O)—NH—CH$_2$—CH$_2$—, —CH$_2$—CH$_2$—C(O)—NH—CH$_2$—, —CH$_2$—CH$_2$—CH$_2$—C(O)—NH—, —C(O)—NH—CH$_2$—CH$_2$—CH$_2$—CH$_2$—, —CH$_2$—C(O)—NH—CH$_2$—CH$_2$—CH$_2$—, —CH$_2$—CH$_2$—C(O)—NH—CH$_2$—CH$_2$—, —CH$_2$—CH$_2$—CH$_2$—C(O)—NH—CH$_2$—, —CH$_2$—CH$_2$—CH$_2$—C(O)—NH—CH$_2$—CH$_2$—, —CH$_2$—CH$_2$—C(O)—NH—, —C(O)—O—CH$_2$—, —CH$_2$—C(O)—O—CH$_2$—, —CH$_2$—CH$_2$—C(O)—O—CH$_2$—, —C(O)—O—CH$_2$—CH$_2$—, —NH—C(O)—CH$_2$—, —CH$_2$—NH—C(O)—CH$_2$—, —CH$_2$—CH$_2$—NH—C(O)—CH$_2$—, —NH—C(O)—CH$_2$—CH$_2$—, —CH$_2$—NH—C(O)—CH$_2$—CH$_2$—, —CH$_2$—CH$_2$—NH—C(O)—CH$_2$—CH$_2$—, —C(O)—NH—CH$_2$—, —C(O)—NH—CH$_2$—CH$_2$—, —O—C(O)—NH—CH$_2$—, —O—C(O)—NH—CH$_2$—CH$_2$—, —NH—CH$_2$—, —NH—CH$_2$—CH$_2$—, —CH$_2$—NH—CH$_2$—, —CH$_2$—CH$_2$—NH—CH$_2$—, —C(O)—CH$_2$—, —C(O)—CH$_2$—CH$_2$—, —CH$_2$—C(O)—CH$_2$—, —CH$_2$—CH$_2$—C(O)—CH$_2$—, —CH$_2$—C(O)—CH$_2$—CH$_2$—, —CH$_2$—CH$_2$—C(O)—CH$_2$—CH$_2$—, —CH$_2$—CH$_2$—C(O)—, —CH$_2$—CH$_2$—CH$_2$—C(O)—NH—CH$_2$—

$CH_2-NH-$, $-CH_2-CH_2-CH_2-C(O)-NH-CH_2-CH_2-NH-C(O)-$, $-CH_2-CH_2-CH_2-C(O)-NH-CH_2-CH_2-NH-C(O)-CH_2-$, $-CH_2-CH_2-CH_2-C(O)-NH-CH_2-CH_2-NH-C(O)-CH_2-CH_2-$, $-O-C(O)-NH-(CH_2)_h-(OCH_2CH_2)_j-$, $-NH-C(O)-O-(CH_2)_h-(OCH_2CH_2)_j-$, $-C(O)-NH-(CH_2)_h-NH-C(O)-$, $-NH-C(O)-NH-(CH_2)_h-NH-C(O)-$, $-O-C(O)-NH-(CH_2)_h-NH-C(O)-$, $-O-$, $-S-$, $-N(R_6)-$, and combinations of two or more of any of the foregoing, wherein (h) is an integer from zero to six, (j) is an interger from zero to 20, and $R_6$ is H, alkyl, substituted alkyl, alkenyl, substituted alkenyl, alkynyl, substituted alkynyl, aryl, or substituted aryl.

15. The water-soluble polymer of claim 1, wherein $X_3$ is selected from the group consisting of $-CH_2-$, $-CH_2-CH_2-$, $-CH_2-CH_2-CH_2-$, and $-CH_2-CH_2-CH_2-CH_2-$.

16. The water-soluble polymer of claim 1, wherein Z comprises an electrophile.

17. The water-soluble polymer of claim 1, wherein Z comprises a nucleophile.

18. The water-soluble polymer of claim 1, wherein Z is selected from the group consisting of hydroxyl (—OH), ester, orthoester, carbonate, acetal, aldehyde, aldehyde hydrate, ketone, vinyl ketone, ketone hydrate, thione, thione hydrate, hemiketal, sulfur-substituted hemiketal, ketal, alkenyl, acrylate, methacrylate, acrylamide, sulfone, amine, hydrazide, thiol, thiol hydrate, carboxylic acid, isocyanate, isothiocyanate, maleimide succinimide

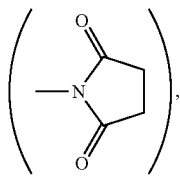, benzotriazole vinylsulfone, chloroethylsulfone, dithiopyridine, vinylpyridine, iodoacetamide, epoxide, glyoxals, diones, mesylates, tosylates, thiosulfonate, tresylate, and silane.

19. The polymer of claim 1, selected from the group consisting of:

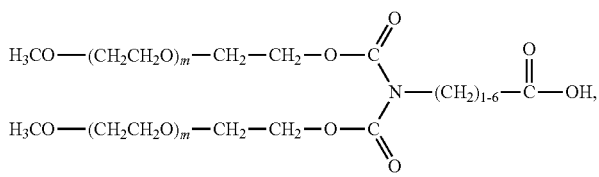

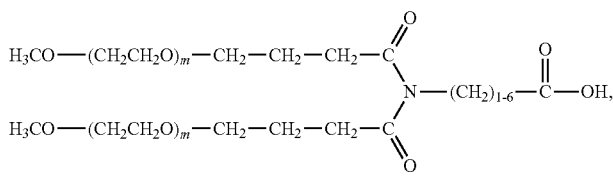

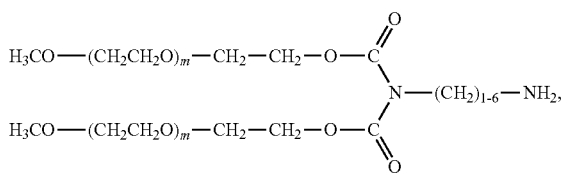

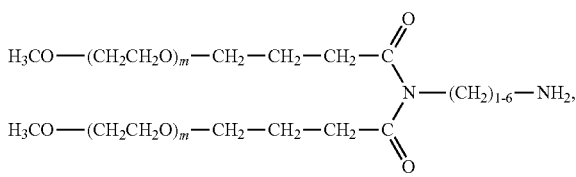

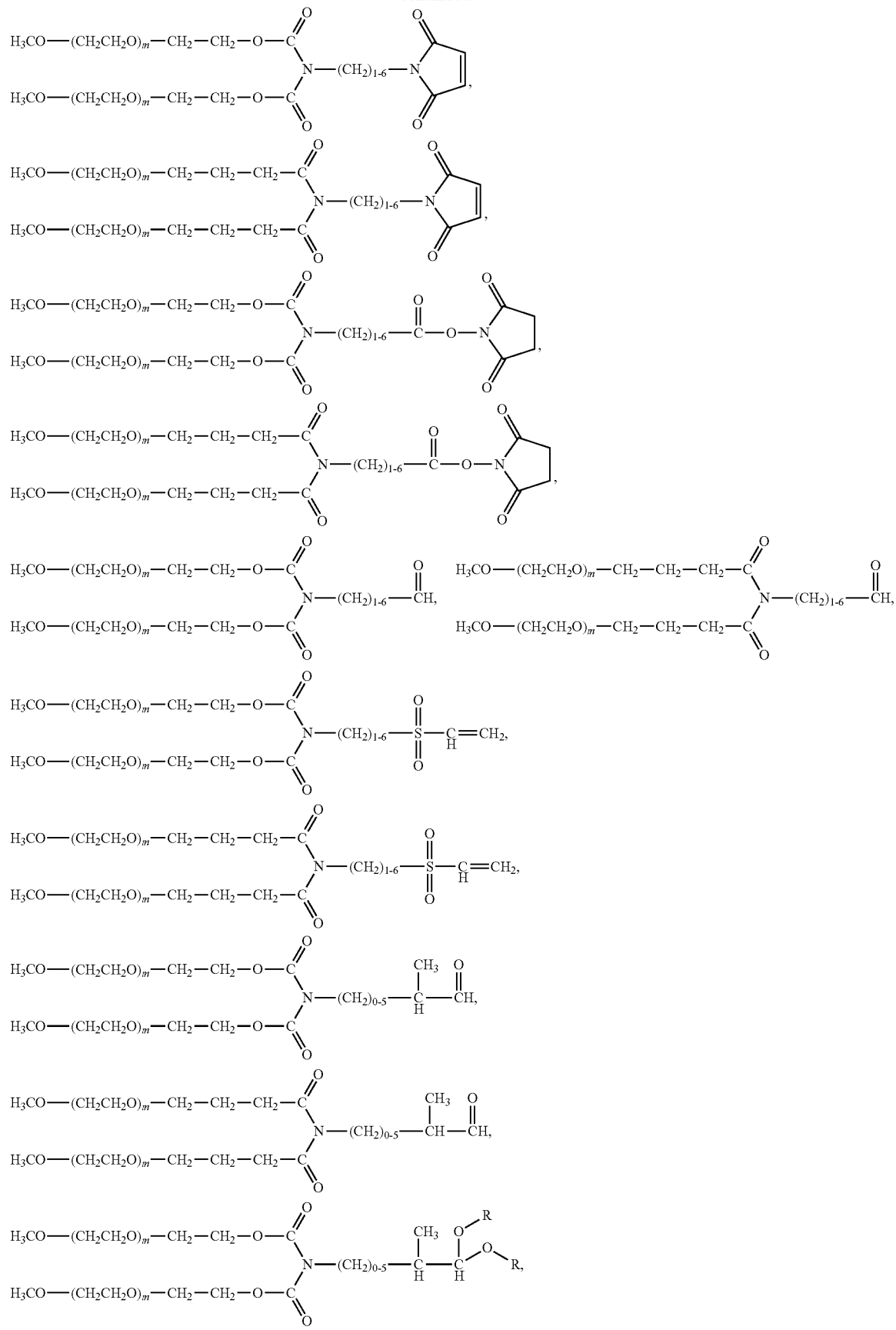

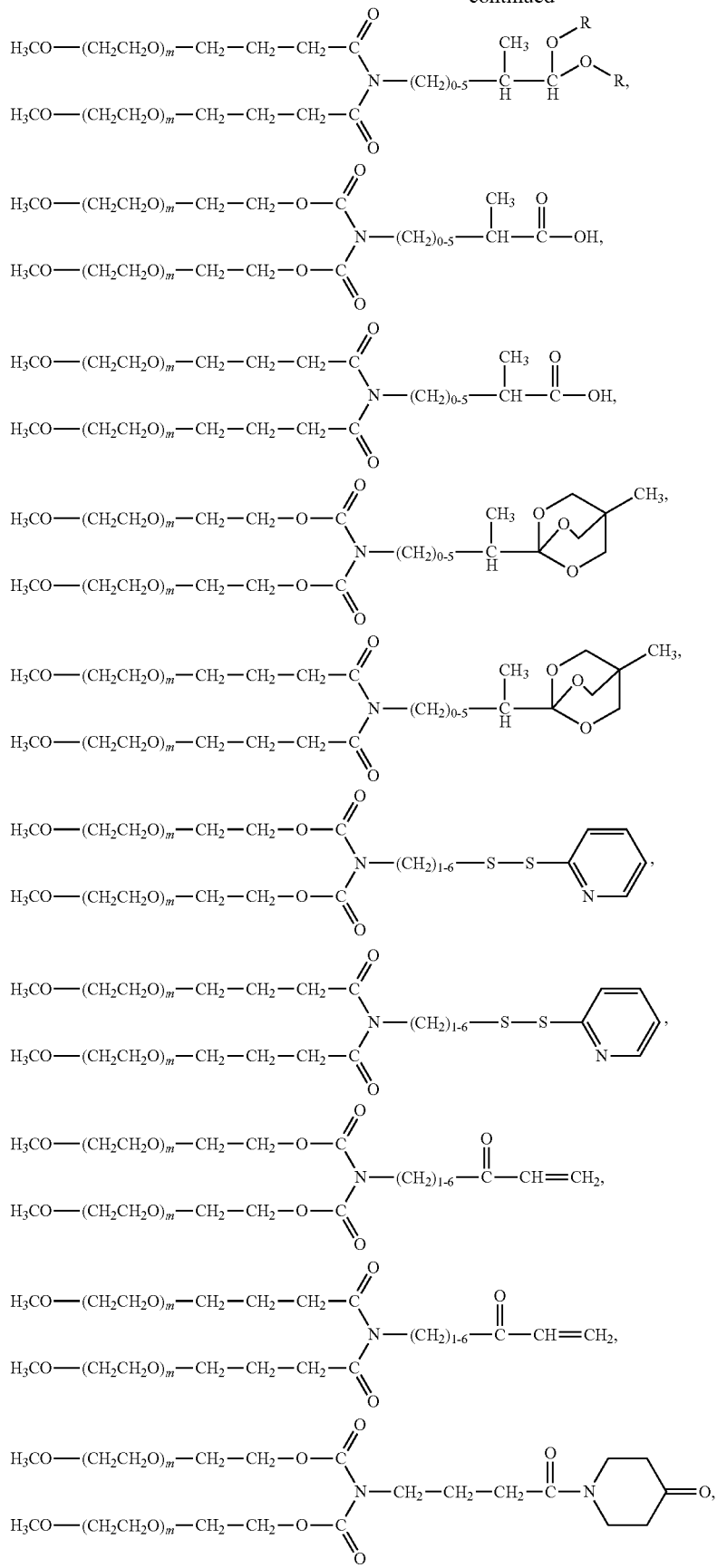

-continued

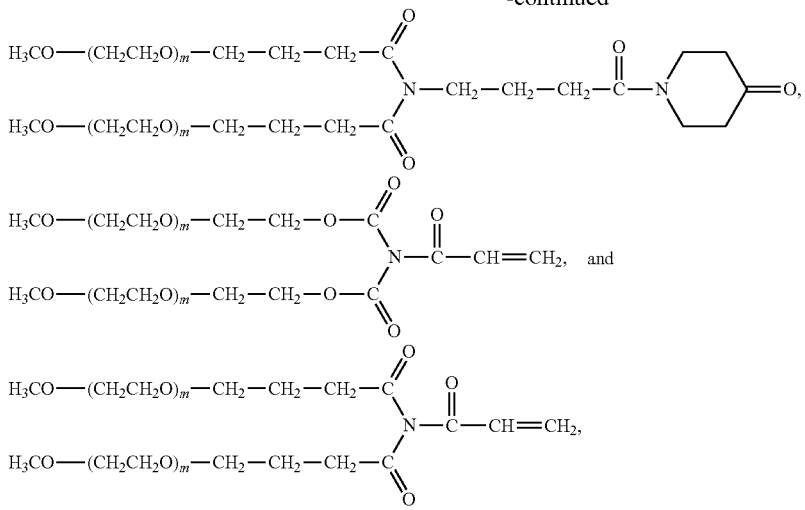

wherein each (m) is independently an integer from 2 to 4,000 and R is C1-C6 alkyl.

20. The polymer of claim 19, selected from the group consisting of:

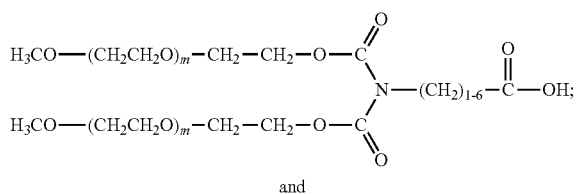

and

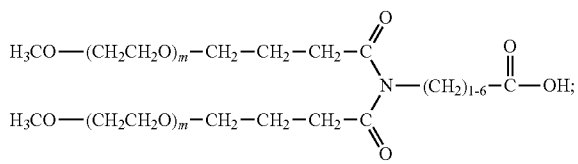

21. A conjugate of Formula II:

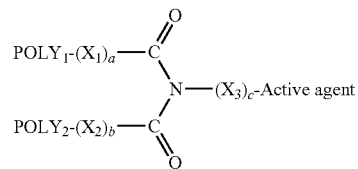

Formula II wherein:
POLY$_1$ is a first poly(ethylene glycol) segment;
POLY$_2$ is a second poly(ethylene glycol) segment;
each of (a) and (b) are independently either zero or one;
(c) is one;
X$_1$, when present, is a first spacer moiety;
X$_2$, when present, is a second spacer moiety;
X$_3$ is a third spacer moiety selected from a C1-C10 alkylene group, and
Active agent represents a residue of a pharmacologically active agent.

22. The conjugate of claim 21, selected from the group consisting of:

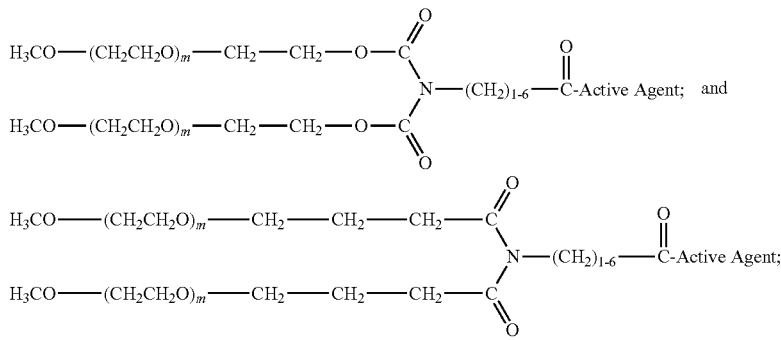

wherein each (m) is independently an integer from 2 to 4,000.

* * * * *